US008748118B2

(12) United States Patent
Cohen et al.

(10) Patent No.: US 8,748,118 B2
(45) Date of Patent: Jun. 10, 2014

(54) URINARY BIOMARKERS FOR CANCER DIAGNOSIS

(75) Inventors: Irun R. Cohen, Rehovot (IL); Meirav Pevsner-Fischer, Rehovot (IL); David Margel, Rehovot (IL); Jack Baniel, Ramat Gan (IL); Ofer Yossepowitch, Ramat Hasharon (IL)

(73) Assignees: Yeda Research and Development Co. Ltd., Rehovot (IL); Mor—Research Applications Ltd., Tel Aviv (IL)

( * ) Notice: Subject to any disclaimer, the term of this patent is extended or adjusted under 35 U.S.C. 154(b) by 0 days.

(21) Appl. No.: 13/388,613

(22) PCT Filed: Aug. 3, 2010

(86) PCT No.: PCT/IL2010/000626
§ 371 (c)(1),
(2), (4) Date: Mar. 2, 2012

(87) PCT Pub. No.: WO2011/016031
PCT Pub. Date: Feb. 10, 2011

(65) Prior Publication Data
US 2012/0149043 A1   Jun. 14, 2012

Related U.S. Application Data

(60) Provisional application No. 61/230,763, filed on Aug. 3, 2009.

(51) Int. Cl.
*G01N 33/574* (2006.01)
*G01N 33/48* (2006.01)

(52) U.S. Cl.
CPC .. *G01N 33/57434* (2013.01); *G01N 2333/5428* (2013.01); *G01N 2333/545* (2013.01); *G01N 33/57407* (2013.01); *G01N 2333/5437* (2013.01)
USPC .......................................... 435/7.94; 435/6.14

(58) Field of Classification Search
None
See application file for complete search history.

(56) References Cited

U.S. PATENT DOCUMENTS

| | | | |
|---|---|---|---|
| 4,313,734 A | 2/1982 | Leuvering | |
| 4,632,901 A | 12/1986 | Valkirs | |
| 4,786,589 A | 11/1988 | Rounds | |
| 5,221,612 A | 6/1993 | Zhau | |
| 5,656,448 A | 8/1997 | Kang | |
| 6,261,791 B1 | 7/2001 | Reiter | |
| 6,280,956 B1 | 8/2001 | Getzenberg | |
| 6,811,995 B1 | 11/2004 | Moses | |
| 7,332,290 B2 | 2/2008 | Rubin | |
| 2004/0126775 A1 | 7/2004 | Altieri | |
| 2005/0196795 A1 | 9/2005 | Siegler | |
| 2006/0068434 A1 | 3/2006 | Stoerker | |
| 2008/0206139 A1 | 8/2008 | Connor | |
| 2009/0123371 A1 | 5/2009 | Debinski | |
| 2009/0136972 A1 | 5/2009 | Moussa | |

FOREIGN PATENT DOCUMENTS

| | | |
|---|---|---|
| EP | 0125118 B2 | 11/1984 |
| WO | 2004/033641 A1 | 4/2004 |
| WO | 2009/029601 A1 | 3/2009 |
| WO | 2009029601 | 3/2009 |

OTHER PUBLICATIONS

Thermo Scientific Human IL-13 ELISA Kit; 2000.*
Human IL-13 ELISA Kit, 2000.*
Kurien et al, Lab Animals, 2004; vol. 38, pp. 333-361.*
Lang et al, Journal of the American Society of Nephrology , 2005; vol. 16, pp. 383-391.*
International Search Report for PCT/IL2010/000626 dated Jul. 11, 2011, 9 pages.
Written Opinion for PCT/IL2010/000626, dated Jul. 11, 2011, 8 pages.
Andriole, Gerald L. et al., (2009) Mortality results from a randomized prostate-cancer screening trial. N Engl J Med 360(13):1310-1319.
Bohle, A. et al., (1990) Elevations of cytokines interleukin-1, interleukin-2 and tumor necrosis factor in the urine of patients after intravesical *Bacillus* Calmette-Guerin immunotherapy. J Urol 144(1):59-64.
Brown, Keith D. et al., (1989) A family of small inducible proteins secreted by leukocytes are members of a new superfamily that include leukocyte and fibroblast-derived inflammatory agents, growth factors, and indicators of various activation processes. J Immunol 142(2):679-687.
Cai, Tommaso et al., (2007) Interleukin-6/10 ratio as a prognostic marker of recurrence in patients with intermediate risk urothelial bladder carcinoma. J Urol 178(5):1906-1912 Epub Sep. 17, 2007.
Cappello, Francesco et al., (2008) Hsp60 expression, new locations, functions and perspectives for cancer diagnosis and therapy. Cancer Biol Ther 7(6):801-809 Epub May 13, 2003.
Cardillo, Maria Rosaria and Ippoliti, Flora (2006) IL-6, IL-10 and HSP-90 expression in tissue microarrays from human prostate cancer assessed by computer-assisted image analysis. Anticancer Res 26(5A):3409-3416.
Ciocca, Daniel R. (1993) Heat shock protein hsp70 in patients with axillary lymph node-negative breast cancer: prognostic implications. J Natl Cancer Inst 85(7):570-574.
Damber, Jan-Erik and Aus, Gunnar (2008) Prostate cancer. Lancet 371(9625):1710-1721.
Esuvaranathan, K. et al., (1995) Interleukin-6 production by bladder tumors is upregulated by BCG immunotherapy. J Urol 154(2 Pt 1):572-575.

(Continued)

*Primary Examiner* — Joanne Hama
*Assistant Examiner* — Fozia Hamud
(74) *Attorney, Agent, or Firm* — Browdy and Neimark, PLLC

(57) ABSTRACT

The present invention is directed to the field of cancer diagnosis, specifically to the diagnosis of bladder cancer (BC) and prostate cancer (CaP). More specifically, the invention provides simple, non-invasive urinary tests characterized by high sensitivity and specificity, wherein urinary levels of heat shock proteins and anti-inflammatory cytokines are used as biomarkers.

26 Claims, 10 Drawing Sheets

(56) References Cited

OTHER PUBLICATIONS

Fleischmann, Jonathan D. et al., (1989) Urinary interleukins in patients receiving intravesical *Bacillus* Calmette-Guerin therapy for superficial bladder cancer. Cancer 64(7):1447-1454.

Fuller, K. J. et al., (1994) Cancer and the heat shock response. Eur J Cancer 30A(12):1884-1891.

Glaessgen, Axel et al., (2008) Heat shock proteins 27, 60 and 70 as prognostic markers of prostate cancer. APMIS 116(10):888-895.

Helmy, Amira et al., (2007) The role of TGF-beta-1 protein and TGF-beta-R-1 receptor in immune escape mechanism in bladder cancer. MedGenMed 9(4):34.

Kapp, Ursula et al., (1999) Interleukin 13 is secreted by and stimulates the growth of Hodgkin and Reed-Sternberg cells. J Exp Med189(12):1939-1946.

Kaufmann, Stefan H. E. (1990) Heat shock proteins and the immune response. Immunol Today 11(4):129-136.

Koçak, Hilmet et al., (2004) Determination of diagnostic and prognostic values of urinary interleukin-8, tumor necrosis factor-alpha, and leukocyte arylsulfatase-A activity in patients with bladder cancer. Clin Biochem 37 (8):673-678.

Lebret, Thierry et al., (2003) Heat shock proteins HSP27, HSP60, HSP70, and HSP90: expression in bladder carcinoma. Cancer 98(5):970-977.

Lebret, Thierry et al., (2007) HSP90 expression: a new predictive factor for BCG response in stage Ta-T1 grade 3 bladder tumours. Eur Urol 51(1):161-166; discussion 166-167.

Levine, Arnold J. et al., (1991) Momand J, Finlay CA. The p53 tumour suppressor gene. Nature 351(6326):453-456.

Lin, Wan-Wan and Karin, Michael (2007) A cytokine-mediated link between innate immunity, inflammation, and cancer. J Clin Invest 117(5):1175-1183.

Lindquist, S. Craig, E. A. (1988) The heat-shock proteins. Annu Rev Genet 22:631-677.

Loskog, Angelica et al., (2007) Human bladder carcinoma is dominated by T-regulatory cells and Th1 inhibitory cytokines. J Urol 177(1):353-358.

Malekzadeh, Kianoosh et al., (2010) Overexpression of IL-13 in patients with bladder cancer. Cancer Invest 28(2):201-207.

McDavid, Kathleen et al., (2004) Prostate cancer incidence and mortality rates and trends in the United States and Canada, Public Health Rep. 119 (2):174-186.

McKenzie, A. N. J. (1993) Interleukin 13, a T-cell-derived cytokine that regulates human monocyte and B-cell function. Proc Natl Acad Sci U S A 90(8):3735-3739.

Minty, A et al., (1993) Interleukin-13 is a new human lymphokine regulating inflammatory and immune responses. Nature 362(6417):248-250.

Pepe, Margaret Sullivan et al., (2001) Phases of biomarker development for early detection of cancer. J Natl Cancer Inst 93(14):1054-1061.

Punnonen, Juha et al., (1993) Interleukin 13 induces interleukin 4-independent IgG4 and IgE synthesis and CD23 expression by human B cells. Proc Natl Acad Sci U S A 90(8):3730-3734.

Quintana, Francisco J. (2000) Vaccination with empty plasmid DNA or CpG oligonucleotide inhibits diabetes in nonobese diabetic mice: modulation of spontaneous 60-kDa heat shock protein autoimmunity. J Immunol 165 (11):6148-6155.

Raz, Itamar et al., (2001) Beta-cell function in new-onset type 1 diabetes and immunomodulation with a heat-shock protein peptide (DiaPep277): a randomised, double-blind, phase II trial. Lancet 358(9295):1749-1753.

Saint, Fabien et al., (2001) T helper 1/2 lymphocyte urinary cytokine profiles in responding and nonresponding patients after 1 and 2 courses of *Bacillus* Calmette-Guerin for superficial bladder cancer. J Urol 166(6):2142-2147.

Saint, Fabien et al., (2002) Prognostic value of a T helper 1 urinary cytokine response after intravesical *Bacillus* Calmette-Guerin treatment for superficial bladder cancer. J Urol 167(1):364-367.

Satyam, A. et al., (2009) A disproportion of T(H)1/T(H)2 cytokines with predominance of T(H)2, in urothelial carcinoma of bladder. Urol Oncol 29(1):58-65 Epub Oct. 17, 2009.

Schmid-Grendelmeier, Peter et al., (2002) Eosinophils express functional IL-13 in eosinophilic inflammatory diseases. J Immunol 169(2):1021-1017.

Schröder, F. H. et al., (2009) Screening and prostate-cancer mortality in a randomized European study. N Engl J Med. 360(13):1320-1328 Epub Mar. 18, 2009.

Sheryka, Elinora et al., (2003) Urinary interleukin-8 levels are elevated in subjects with transitional cell carcinoma. Urology 62(1):162-166.

Skinnider, Brian F. et al., (2001) Interleukin 13 and interleukin 13 receptor are frequently expressed by Hodgkin and Reed-Sternberg cells of Hodgkin lymphoma. Blood 97(1):250-255.

Terabe, Masaki et al., (2000) NKT cell-mediated repression of tumor immunosurveillance by IL-13 and the IL-4R-STAT6 pathway. Nat Immunol 1(6):515-520.

Urushibara, Masayasu et al., (2007) HSP60 may predict good pathological response to neoadjuvant chemoradiotherapy in bladder cancer. Jpn J Clin Oncol 37(1):56-61.

Van Rhijn, Bas W. G. et al., (2005) Urine markers for bladder cancer surveillance: a systematic review. Eur Urol 47 (6):736-748 Epub Mar. 23, 2005.

Watson, R (2003) Heat shock proteins in the genitourinary system. Curr Urol Reports 4(1):70-76.

\* cited by examiner

URINARY BIOMARKERS FOR CANCER DIAGNOSIS

CROSS REFERENCE TO RELATED APPLICATION

This application is a U.S. National Stage Entry filing of and claims priority benefit from International Patent Application No. PCT/IL2010/000626, filed 3 Aug. 2010, now published as WO 2011/016031, which in turn claims priority benefit from U.S. Provisional Patent Application No. 61/230,763, filed 3 Aug. 2009, both of which are incorporated herein by reference in their entirety.

FIELD OF THE INVENTION

The present invention is directed to the field of cancer diagnosis, specifically the diagnosis of genitourinary cancer such as bladder cancer and prostate cancer. More specifically, the invention provides diagnostic methods comprising determining the levels of urinary heat shock proteins and cytokines.

BACKGROUND OF THE INVENTION

Bladder cancer (BC) is one of the most common malignancies in developed countries, ranking as the sixth most frequent neoplasm. The disease exists in two main forms: non-invasive BC, which lacks invasion into surrounding muscle tissue and is the more common form accounting for 75% of all cases, and muscle invasive BC, in which the tumor spreads into the urinary bladder muscle and may metastasize.

The gold standard for detection of BC is cystoscopy; however, this procedure is invasive, uncomfortable, costly and may provoke urinary tract infection. Moreover, cystoscopy may miss certain lesions, in particular small areas of carcinoma in situ. Currently, cytology is the only established non-invasive adjunct to cystoscopy. Although cytology is sensitive (70-80%) and highly specific (90-95%) for the diagnosis of high-grade BC, sensitivity is as low as 6-38% for detecting low-grade tumors (Bastacky et al., 1999).

In BC patients, urine is constantly in close contact with tumor cells and the urothelium surrounding them. Therefore it has been suggested that biomarkers in the urine or in tumor cells isolated from urine samples could be helpful for detecting and monitoring BC. Among the studied markers, several assays have been approved by the US FDA, including Bladder tumor antigen (BTA), BTA stat, Fibrin degradation products (FDP), Nuclear Matrix protein 22 (NMP-22), Immunocyt and FISH (Urovysion) (van Rhijn et al., 2005). Most of these assays manifest a higher overall sensitivity for BC compared to urine cytology, but their specificity is much less (van Rhijn et al., 2005): urinary tract infection, benign prostatic hypertrophy and renal calculi can affect these assays. Various other tests have been developed in the effort to identify biochemical markers that may have diagnostic and prognostic value, including tests to identify tumor-associated markers in the urine, serum, and bladder cancer tissue specimens. For example, urinary immunoglobulins have been found to increase in persons who have bladder cancer and appear to have some diagnostic and prognostic value. Other suggested markers are disclosed, for example, in U.S. Pat. No. 5,221,612, U.S. Pat. No. 7,332,290, U.S. Pat. No. 6,811,995 U.S. Pat. No. 6,280,956, U.S. Pat. No. 6,261,791, U.S. 20050196795, U.S. 20040126775, U.S. 20090136972 and WO 2004/0033641. To date, there is no consensus regarding the relevance of these tests and their role in enhancing or replacing cystoscopy.

The routine use of prostate-specific antigen (PSA) as a screening tool since the early 1990's has had a deep impact on early diagnosis of prostate cancer (CaP) and has resulted in an increase in CaP detection (McDavid et al., 2004). However, the use of PSA is currently being debated since it is not clear if PSA screening has led to a decline in mortality due to CaP (Andriole et al., 2009; Schroder et al., 2009). In addition, the vast amount of unnecessary biopsies due to false-positive PSA results places a large burden on the healthcare system and leads to patient discomfort (Damber et al., 2008). As a result, there is a need for more specific and more sensitive biomarkers for CaP.

Cancer is associated with local inflammation (Lin et al., 2007). Among the many known factors suggested to mediate or regulate various aspects of inflammatory reactions are heat shock proteins and cytokines.

Heat Shock Proteins (HSPs) are a class of functionally related proteins whose expression is increased when cells are exposed to elevated temperature or other stress (Lindquist et al., 1988). In neoplasms, the expression of HSPs is implicated in the regulation of apoptosis, as a modulator of p53, in the immune response against tumors, and in multidrug resistance (Kaufmann et al., 1990; Levine et al., 1991; Ciocca et al., 1993; Cappello et al., 2008), and HSP expression was found to be altered in certain tumors (Fuller et al., 1994). Recently, the expression of HSPs in tumor biopsy material particularly HSP60 and HSP90 were proposed as prognostic factors in BC. Using immunohistochemical staining, Lebert et al, showed that decreased expression of these HSPs in the tumor is correlated with invasive BC (Lebret et al., 2003). In addition, it was found that low HSP90 expression predicted failure of immunotherapy (Lebret et al., 2007).

Secretion of immunosuppressive cytokines is a non-specific strategy for tumor immune evasion in many malignancies. Thus far, studies addressing cytokine expression in bladder cancer focused on the immune response to Bacillus Calmette-Guérin (BCG) immunotherapy (Bohle et al., 1990; Fleischmann et al., 1989; Saint et al., 2001).

Certain studies report the detection of cytokines such as Interleukin (IL)-6, IL-8 and IL-10 in the urine of BC patients. Kochac et al. (2004) and Sheryka et al. (2003) suggest that urinary IL-8 levels are elevated in patients with invasive BC. These studies did not differentiate between newly diagnosed BC patients and patients that have been treated with intravesical or other anti-cancer therapy, known to affect urinary cytokine levels. Esuvaranathan et al. (1995), aiming to evaluate the effect of BCG treatment on urinary cytokine levels, report that urinary IL-6 levels are elevated in some of the BC patients. Cai et al. (2007) attempted to find an association between urinary levels of IL-6/IL-10 and recurrent BC. The authors indicated that no difference was found between the IL-6/IL-10 ratio of control subjects and of patients with initial BC.

Loskog et al (2007) demonstrated that bladder cancer tissue is infiltrated by regulatory T-cells expressing large amounts of TGF-β and IL-10 mRNA. They further confirmed that circulating T cells of these patients were unresponsive to polyclonal T cell activation compared to healthy controls. Helmy et al (2007), using immunelectromicroscopy, reported the expression of TGF-β protein in exfoliated malignant epithelial (urothelial) cells in the urine of patients with BC.

Cardillo and Ippoliti (2006) reported that IL-6, IL-10 and HSP90 immunoreactivity was higher in prostatic carcinoma (CaP) and intra-epithelial prostatic neoplasia than in normal prostatic tissue adjacent to neoplasia, and therefore, changes in their expression in human CaP samples could be used as a prognostic marker of disease progression.

IL-13 was originally described as a T cell-derived cytokine that inhibits inflammatory cytokine production (Minty et al., 1993; McKenzie et al., 1993; Punnonen et al., 1993) secreted from immune cells (Schmid-Grendelmeier et al., 2002; Brown et al., 1989). Though this original description remains accurate, the known functions of IL-13 have expanded over the past few years. In cancer, IL-13 inhibits $CD8^+$ CTL-mediated tumor immunosurveillance (Terabe et al., 2000) and contributes to tumor escape from apoptosis and growth arrest (Skinnider et al., 2001; Kapp et al., 1999). Type I diabetic patients treated with HSP60 derived peptide, showed lesser need for exogenous insulin that was positively correlated with IL-13 production by T-cells, thereby indicating its importance as an anti-inflammatory mediator (Raz et al., 2001). A recent case-control study demonstrated a highly significant difference in mRNA and protein expression of IL-13 between patients with bladder cancer and controls (MalekZadeh et al., 2010; published after the priority date of the present invention).

To date, no cytokine or HSP urinary marker is known to differentiate between BC-afflicted subjects and subjects presenting with hematuria due to benign pathology, thus having adequate reliability to be used in clinical diagnosis. There remains an unmet need for improved compositions and methods for providing early diagnosis of genitourinary cancer such as bladder cancer or prostate cancer and for determining disease staging and prognosis.

SUMMARY OF THE INVENTION

The present invention provides compositions, methods and kits for diagnosing cancer, specifically the diagnosis of genitourinary cancer such as bladder cancer (BC) and prostate cancer (CaP). More specifically, the invention provides simple, non-invasive urinary tests, with high sensitivity and specificity for BC and CaP, wherein urinary levels of heat shock proteins and anti-inflammatory cytokines are used as biomarkers.

The present invention is based in part on unexpected results obtained when testing the levels of protein antigens in unsedimented urine samples obtained from bladder cancer patients and control individuals. A distinct set of antigens comprising certain heat shock proteins (HSPs) and cytokines was identified, which accurately correlates with the clinical diagnosis of these patients compared to controls. Moreover, the identified antigen markers could differentiate between low-grade, non-muscle invasive disease (non-MI-BC), and high-grade, muscle invasive tumors (MI-BC). Surprisingly, in contradistinction with previously tested urinary biomarkers, the marker antigens of the invention specifically and accurately discriminate not only between BC patients and healthy control subjects, but also between BC patients and patients afflicted with non-malignant conditions accompanied by hematuria, which present with blood components in the urine. The inventors have also identified urinary biomarkers for CaP, having increased sensitivity and specificity compared to the currently used PSA test for CaP.

Thus, the present invention provides compositions, methods and kits for diagnosing genitourinary cancer. The compositions, methods and kits of the invention are unexpectedly useful also for diagnosing the cancer stage or grade. According to certain embodiments, the invention provides methods for diagnosing bladder cancer in a subject, comprising determining the levels of anti-inflammatory cytokines and/or HSPs in a urine sample obtained from the subject. In various embodiments, the methods comprise determining the levels of at least one biomarker selected from the group consisting of IL-6, IL-8, IL-10, IL-13, TGF-β, HSP60, HSP70 and HSP90. In other embodiments, the methods comprise determining the levels of a plurality of these biomarkers, e.g. 2, 3, 4 or more of the above-specified biomarkers. Each possibility is a separate embodiment of the invention.

According to one aspect of the present invention, there is provided a method for assessing (or determining) the presence or absence of bladder cancer in a subject, comprising determining the level of at least one biomarker selected from the group consisting of IL-13, IL-10, HSP60, HSP70 and HSP90 in a urine sample obtained from the subject, wherein a significant elevation in the level of the at least one biomarker compared to a control value corresponding to a healthy individual indicates that said subject is afflicted with bladder cancer. In one embodiment, the subject is suspected of having bladder cancer. Each possibility is a separate embodiment of the invention.

In another embodiment, the biomarkers are selected from the group consisting of IL-13, IL-10 and HSP60. In yet another embodiment, the biomarkers are selected from the group consisting of IL-13 and HSP60. In another particular embodiment, the biomarker is IL-13. Each possibility is a separate embodiment of the invention.

In another embodiment, the method comprises determining the levels of a plurality of biomarkers. For example, the method comprises determining the levels of two, three, four or more of the biomarkers of the invention, e.g. of the biomarkers selected from the group consisting IL-13, IL-10, IL-8, HSP60, HSP70 and HSP90. Optionally and preferably, the levels of at least one heat shock protein and at least one cytokine are measured. In a particular embodiment, the biomarkers are IL-13 and HSP60. Each possibility is a separate embodiment of the invention.

In another embodiment, the control value corresponding to a healthy individual corresponds to the value in a urine sample obtained from an individual not afflicted with bladder cancer, e.g. a healthy individual not afflicted with or diagnosed with a disease or an individual afflicted with a non-malignant pathology of the urinary tract (e.g. patients identified with hematuria from benign causes such as stone disease or benign prostatic hyperplasia). In some embodiments, the healthy individual is not afflicted with a genitourinary infection or inflammatory disease, e.g. urinary tract infection. In other embodiments, the control value may correspond, for example, to a panel of control samples from a set of healthy individuals, or a stored set of data corresponding to control individuals (e.g. healthy individuals or individuals that are not afflicted with cancer or infection). Each possibility is a separate embodiment of the invention.

In other embodiments, the cancer is selected from the group consisting of transitional cell carcinoma, squamous cell carcinoma and adenocarcinoma. In a particular embodiment, the cancer is transitional cell carcinoma. In another embodiment, the subject is symptomatic. In another embodiment, the subject is asymptomatic. Each possibility is a separate embodiment of the invention.

According to other embodiments, the methods of the invention are useful for discriminating between superficial and invasive bladder cancer or for determining the stage or grade of the tumor. In some embodiments, elevated levels of HSP60, HSP70, HSP90, IL-8, IL-13, IL-6 and/or TGF-β may be indicative for high grade and/or invasive tumors. Thus, in another aspect, the invention provides a method for assessing (or determining) the presence or absence of muscle invasive bladder cancer in a subject, comprising determining the level of at least one biomarker selected from the group consisting of HSP60, HSP70 and HSP90 in a urine sample obtained from the subject, wherein a significant elevation in the level of the at least one biomarker compared to a control value (e.g. a value corresponding to a subject having non-invasive BC) indicates that said subject is afflicted with muscle invasive bladder cancer. In another embodiment, the method is useful for determining the presence or absence of muscle invasion in a subject diagnosed with (or suspected of having) bladder cancer. Each possibility is a separate embodiment of the invention.

In a particular embodiment, the biomarker is HSP60. In another embodiment, the method comprises determining the levels of a plurality of the biomarkers of the invention biomarkers (e.g., two or three biomarkers) selected from the group consisting of HSP60, HSP70, HSP90, IL-8, IL-13, IL-6 and TGF-β. In another embodiment, the method involves determining the levels of HSP60, HSP70 and HSP90 in the sample. Each possibility is a separate embodiment of the invention.

The control value may be, for example, a sample obtained from an individual having non-invasive bladder cancer (e.g. low-stage bladder cancer). In other embodiments, the control value may be, for example, corresponding to a panel of control samples obtained from individuals having non-muscle invasive cancer, or a stored set of data corresponding to control individuals (e.g., afflicted with non-invasive bladder cancer). In some embodiments, the control value is obtained from individual (or individuals) not afflicted with a genitourinary infection or inflammatory disease.

In another aspect, the invention provides a method for diagnosing bladder cancer in a subject suspected of having bladder cancer, comprising: determining the level of IL-13, HSP60, HSP70 and HSP90 in a urine sample obtained from the subject, wherein:
   i. a significant elevation in the level of IL-13 in the sample compared to a negative control value corresponding to a healthy individual indicates that said subject is afflicted with bladder cancer; and
   ii. a significant elevation in the level of HSP60, HSP70 and HSP90 in the sample compared to a positive control value corresponding to an individual having non-invasive bladder cancer indicates that said subject is afflicted with invasive bladder cancer, and a level of HSP60, HSP70 and HSP90 which is not significantly elevated compared to the positive control value indicates that the subject has non-invasive bladder cancer.

According to one particular embodiment, the method determines between muscle invasive BC and non-invasive BC.

In another aspect, the present invention provides a method for assessing the presence or absence of bladder cancer in a subject suspected of having bladder cancer, comprising determining the level of at least one cytokine selected from the group consisting of: IL-13, IL-10 and IL-8, and at least one heat shock protein selected from the group consisting of HSP60, HSP70, HSP90, in a urine sample obtained from the subject, wherein a significant elevation in the level of the at least one cytokine and at least one HSP compared to a control value corresponding to a healthy individual, indicates that said subject is afflicted with bladder cancer.

In another aspect, the invention provides a method for determining the presence or absence of prostate cancer in a subject, comprising determining the level of at least one biomarker selected from the group consisting of IL-13 and IL-1β in a urine sample obtained from the subject, wherein a significant elevation in the level of the at least one biomarker compared to a control value corresponding to a healthy individual indicates that said subject is afflicted with prostate cancer. In one embodiment, the subject is suspected of having prostate cancer. In another embodiment, the method comprises determining the level of IL-13. In another embodiment, the method comprises determining the level of IL-1β. In another embodiment, the method comprises determining the level of IL-13 and IL-1β. Each possibility is a separate embodiment of the invention.

In another embodiment, the control value corresponding to a healthy individual corresponds to the value in a urine sample obtained from an individual not afflicted with prostate cancer, e.g. a healthy individual not afflicted or diagnosed with a disease, or an individual afflicted with a non-malignant pathology of the urinary tract. In some embodiments, the healthy individual is not afflicted with a genitourinary infection or inflammatory disease. In other embodiments, the control value may correspond, for example, to a panel of control samples from a set of healthy individuals, or a stored set of data corresponding to control individuals (e.g. healthy individuals or individuals that are not afflicted with cancer or infection).

In another embodiment, there is provided a method for diagnosing a genitourinary cancer in a subject in need thereof (e.g., suspected of having genitourinary cancer), comprising determining the level of IL-13 in a urine sample obtained from the subject, wherein a significant elevation in the level of IL-13 compared to a control value corresponding to a healthy individual indicates that said subject is afflicted with genitourinary cancer.

In one embodiment, the cancer is bladder cancer. In certain embodiments, the method further comprises determining the levels of at least one heat shock protein selected from the group consisting of HSP60, HSP70 and HSP90, wherein a significant elevation in the level of at least one HSP compared to a control value corresponding to a healthy individual indicates that said subject is afflicted with bladder cancer. In other embodiments, the method further comprises determining the levels of at least one additional cytokine selected from the group consisting of IL-10 and IL-8, wherein a significant elevation in the level of at least one cytokine selected from IL-10 and IL-8 compared to a control value corresponding to a healthy individual, indicates that said subject is afflicted with bladder cancer. Each possibility is a separate embodiment of the invention.

In another embodiment, the cancer is prostate cancer. In one embodiment, the method further comprises determining the level of IL-1β, wherein a significant elevation in the level of IL-1β compared to a control value corresponding to a healthy individual, indicates that said subject is afflicted with prostate cancer.

Thus, according to one embodiment, the present invention provides a method for diagnosing a genitourinary cancer in a subject in need thereof, comprising determining the level of IL-13 and at least one biomarker selected from the group consisting of HSP60, HSP70, HSP90, IL-10, IL-8 and IL-1β, wherein:
   (i) a significant elevation in the level of IL-13 and at least one biomarker selected from the group consisting of HSP60, HSP70, HSP90, IL-10 and IL-8 compared to a control value corresponding to a healthy individual, indicates that said subject is afflicted with bladder cancer; and
   (ii) a significant elevation in the level of IL-13 and IL-1β compared to a control value corresponding to a healthy individual indicates that said subject is afflicted with prostate cancer.

Conveniently, the methods of the invention are performed using an immunoassay. In one embodiment, the methods of the invention are performed using an enzyme-linked immunosorbent assay (ELISA). In another embodiment, the methods of the invention are performed using a bead flow cytometry assay. In another embodiment, the methods of the invention are performed using a radioimmunoassay (RIA). In another embodiment, the methods of the invention are performed using an antibody microarray chip.

As the methods of the invention are amenable for automation and are thus suitable for medium and large scale screening, they may be used e.g. for screening subjects who may be at risk for developing bladder cancer or prostate cancer, e.g. cigarette smokers or subjects exposed to other risk factors.

In various embodiments, a significant elevation in the level of a biomarker compared to control is indicative of the presence of bladder cancer. In other embodiments, a significant elevation in the level of a biomarker compared to control is indicative of the presence of invasive bladder cancer. In other embodiments, a significant elevation in the level of a biomarker compared to control is indicative of the presence of prostate cancer, as detailed herein.

In the methods of the invention, a "significant elevation" in the level or amount of a urinary biomarker refers, in different embodiments, to a statistically significant elevation, or in other embodiments to a significant elevation as recognized by a skilled artisan. For example, without limitation, the present invention demonstrates that an increase of either 10 ng/ml of HSP60 or 10 pg/ml of IL-13 is associated with more than ten times the chance of BC.

According to certain embodiments, the methods of the invention provide for measuring the levels of biomarkers in a urine sample without the need to isolate or enrich exfoliated tumor cells in the urine sample prior to detection. In one embodiment, the sample is a non-sedimented urine sample. In another embodiment, the urine sample is substantially free of residual cells.

In one embodiment, the urine sample is a voided urine sample. In certain embodiments, the sample is collected from the subject without a preceding step of bladder scraping or washing. In another embodiment, the urine sample is obtained non-invasively. In other embodiments, the urine sample may conveniently be frozen after being collected from the subject and thawed before determining the levels of antigens e.g. by an immunoassay.

According to further aspects the present invention provides kits suitable for use in methods of diagnosing genitourinary cancer in a subject. In one embodiment the kits are suitable for diagnosing bladder cancer in a subject. In another embodiment the kits are suitable for diagnosing prostate cancer in a subject. Thus, in another embodiment, there is provided a diagnostic kit comprising i) means for collecting a urine sample from a subject and ii) means for determining the level of at least one biomarker of the invention in the sample. In a particular embodiment, the at least one biomarker is selected from the group consisting of IL-13, HSP60, HSP70 and HSP90. In certain embodiments, the means for determining the levels of at least one biomarker comprise at least one antibody directed to the biomarkers of the invention (e.g., IL-13, HSP60, HSP70 or HSP90). In another particular embodiment, the means for determining the levels of at least one biomarker comprise at least one antibody directed to at least one biomarker selected from the group consisting of IL-13 and IL-1β.

Other objects, features and advantages of the present invention will become clear from the following description and drawings.

DETAILED DESCRIPTION OF THE INVENTION

Figure 1A:
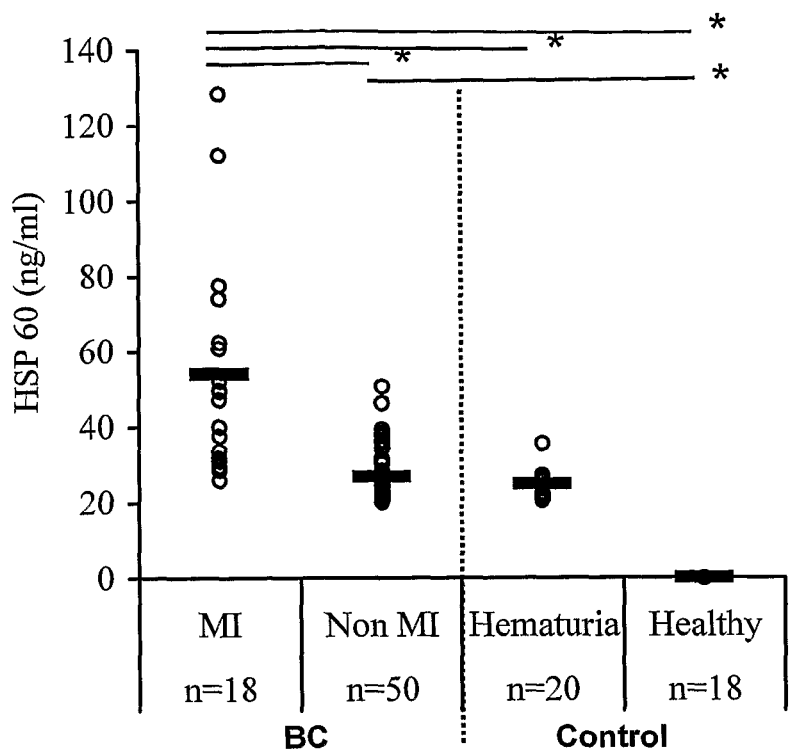
FIG. 1. Urinary concentrations of HSP60 (a), HSP70 (b) and HSP90 (c). Urine was assayed by ELISA for the presence of HSP 60 (a), 70 (b) and 90 (c). The results are presented by a scatter plot—each dot represents one patient. Only one dot is presented when urinary concentrations overlap, the number of overlapping patients is indicated. The mean of each group is presented by a line. *, $p<0.05$ by one-way ANOVA followed by least significant difference (LSD) post-hoc test.

The present invention provides compositions, methods and kits for diagnosing genitourinary cancer, particularly BC or CaP. The compositions, methods and kits of the invention are unexpectedly useful also for diagnosing the stage or grade of the tumor, wherein urinary levels of certain heat shock proteins and cytokines are used as biomarkers. The methods of the invention are useful for diagnosing low-grade, non-muscle invasive bladder cancer and high-grade, muscle invasive bladder cancer as well as for discriminating between these tumor types. Moreover, the methods are useful for differentiating BC patients not only from healthy individuals, but also from patients with hematuria from benign causes.

As exemplified herein below, a distinct set of identified biomarkers accurately correlated with the clinical diagnosis of BC and CaP patients compared to controls. In particular, urinary concentrations of IL-13, IL-10 and IL-8 as well as HSP60, HSP 70 and HSP90 were significantly elevated in patients with BC. Moreover, the urine concentrations of HSP60, HSP70 and HSP90, and IL-13, IL-8, IL-6 and TGF-β cytokines differentiated between low-grade, non-muscle invasive disease (non-MI-BC), and high-grade, muscle invasive tumors (MI-BC). Surprisingly, urinary concentrations of IL-13 and IL-1β were significantly elevated in patients with prostate cancer.

Thus, the present invention provides compositions, methods and kits for diagnosing genitourinary cancer, particularly bladder cancer and prostate cancer, including for diagnosing bladder cancer stage or grade. While certain reports may have detected specific cytokines and/or HSPs in the urine of BC or CaP patients, the present invention relates to, in certain embodiments, determining the levels of a plurality of biomarkers (e.g. 2, 3, 4, 5 or 6 biomarkers of the invention), thereby providing a significantly more accurate and reliable assay in discriminating patients and control subjects than each biomarker alone.

In one embodiment the subject is a mammal, preferably a human. According to certain embodiments, diagnosis of the urinary levels of the biomarkers of the invention may be affected using an immunoassay. The immunoassay is typically characterized by the use of specific binding properties of a particular antibody to isolate, target and/or quantify the antigen (e.g., a biomarker of the invention). For example, an antibody may be synthesized or commercially purchased (as exemplified below) to detect the specific biomarkers of the invention. In one embodiment the IL-13 biomarker has the amino acid sequence as set forth in SEQ ID NO:1 (Accession No: P35225) or a homolog thereof. In another embodiment the IL-6 biomarker has the amino acid sequence as set forth in SEQ ID NO:2 (Accession No: P05231) or homolog thereof. In another embodiment the IL-8 biomarker has the amino acid sequence as set forth in SEQ ID NO:3 (Accession No: P10145) or a homolog thereof. In another embodiment the IL-10 biomarker has the amino acid sequence as set forth in SEQ ID NO:4 (Accession No: P22301) or a homolog thereof. In another embodiment the TGF-β biomarker has the amino acid sequence as set forth in SEQ ID NO:5 (Accession No: P01137) or a homolog thereof. In another embodiment the HSP60 biomarker has the amino acid sequence as set forth in SEQ ID NO:6 (Accession No: P10809) or a homolog thereof In another embodiment the HSP70 biomarker has the amino acid sequence as set forth in SEQ ID NO:7 (Accession No: P08107) or a homolog thereof In another embodiment the HSP90 biomarker has the amino acid sequence as set forth in SEQ ID NO:8 (Accession No: P07900) or a homolog thereof. In another embodiment the IL1-β biomarker has the amino acid sequence as set forth in SEQ ID NO:9 (Accession No: P01584) or a homolog thereof.

The term "homolog" as used herein refers to a polypeptide which having at least 70%, at least 75%, at least 80%, at least 85% or at least 90% identity to the biomarker's amino acid sequence. According to some embodiments, the methods of the invention are capable of diagnosing BC and/or Cap by detecting fragments or derivatives of the biomarkers of the invention (e.g., as listed in SEQ ID NO: 1 to SEQ ID NO: 9).

According to one embodiment, the present invention provides a method for assessing the presence or absence of bladder cancer in a subject, comprising determining the level of at least one biomarker selected from the group consisting of IL-13, IL-10, IL-8, HSP60, HSP70 and HSP90 in a urine sample obtained from the subject, wherein a significant elevation in the level of the at least one biomarker compared to a control value corresponding to a healthy individual indicates that said subject is afflicted with bladder cancer. According to another embodiment, the method comprises determining the level of IL-13 in a urine sample obtained from the subject. According to another embodiment, the method comprises determining the level of IL-10 in a urine sample obtained from the subject. According to another embodiment, the method comprises determining the level of IL-8 in a urine sample obtained from the subject. According to another embodiment, the method comprises determining the level of HSP60 in a urine sample obtained from the subject. According to another embodiment, the method comprises determining the level of HSP70 in a urine sample obtained from the subject. According to another embodiment, the method comprises determining the level of HSP90 in a urine sample obtained from the subject. Each possibility is a separate embodiment of the invention.

According to one embodiment, the method comprises determining the level of at least two biomarkers selected from the group consisting of IL-13, IL-10, IL-8 HSP60, HSP70 and HSP90. The at least two biomarkers may be, for example, two cytokines (e.g., IL-13 and IL-10, or IL-13 and IL-8), two heat shock protein (e.g., HSP60 and HSP70, or HSP60 or HSP90), or alternatively, one cytokine and one heat shock protein (e.g., IL-13 and HSP60 or IL-10 and HSP60). Each possibility is a separate embodiment of the invention. According to another embodiment, the method comprises determining the level of at least three biomarkers, at least four, alternatively, at least five biomarkers selected from the group consisting of IL-13, IL-10, IL-8, HSP60, HSP70 and HSP90. According to another embodiment, the method may comprise determining the levels of two, three, four or more of the biomarkers of the invention, e.g. of the biomarkers selected from the group consisting IL-13, IL-10, IL-8, HSP60, HSP70 and HSP90. Each possibility is a separate embodiment of the invention.

In another embodiment, the invention provides a method for diagnosing bladder cancer in a subject suspected of having bladder cancer, comprising:
 i. determining the level of IL-13 in a urine sample obtained from the subject, wherein a significant elevation in the level of IL-13 in the sample compared to a negative control value corresponding to a healthy individual indicates that said subject is afflicted with bladder cancer; and
 ii. determining the level of HSP60, HSP70 and HSP90 in a urine sample obtained from said subject, wherein a significant elevation in the level of HSP60, HSP70 and HSP90 in the sample compared to a positive control value corresponding to an individual having non-invasive bladder cancer indicates that said subject is afflicted with invasive bladder cancer, and a level of HSP60, HSP70 and HSP90 which is not significantly elevated compared to the positive control value indicates that the subject has non-invasive bladder cancer.

According to one particular embodiment, the method determines between muscle invasive BC and non-invasive BC.

Genitourinary Cancer

Genitourinary cancers account for about 42% of cancers in men (primarily as prostate cancer) and 4% in women. Included within this group are e.g., cancers of the prostate, bladder, urethra and testicles. Despite significant progress in molecular and cellular biology that has helped identify specific molecular pathways that contribute to the biological potential and behavior of genitourinary cancers, current treatments for advanced prostate, urethral and bladder cancers remain limited.

Bladder Cancer

Ninety percent of bladder cancer cases are transitional cell carcinomas (TCC) that arise from the inner lining of the bladder called the urothelium. The other 10% of tumors are squamous cell carcinoma, adenocarcinoma, sarcoma, small cell carcinoma and secondary deposits from cancers elsewhere in the body. The pattern of growth of TCCs can be papillary, sessile (flat) or carcinoma-in-situ (CIS). Most TCC are papillary carcinomas, which tend to be superficial and well-differentiated and to grow outward; sessile tumors are more insidious, tending to invade early and metastasize. Squamous cell carcinomas are less common and usually occur in patients with parasitic bladder infestation or chronic mucosal irritation. Adenocarcinomas may occur as primary tumors or may reflect metastasis from intestinal carcinoma. In certain embodiments, the term "adenocarcinoma" refers to primary adenocarcinoma. In the bladder, carcinoma in situ is high grade but noninvasive and usually multifocal; it tends to recur.

In >40% of patients, tumors recur at the same or another site in the bladder, particularly if tumors are large or poorly differentiated or if several tumors are present. Bladder cancer tends to metastasize to the lymph nodes, lungs, liver, and bone.

Most BC patients present with unexplained hematuria (gross or microscopic). Some patients present with anemia, and hematuria is detected during evaluation. Irritative voiding symptoms (dysuria, burning, frequency) and pyuria are also common at presentation. Pelvic pain occurs with advanced cancer, when a pelvic mass may be palpable. According to certain embodiments, a "subject suspected of having bladder cancer" indicates that the subject presents one or more symptoms or signs characteristic of BC. According to certain embodiments, the subject may have at least one symptom selected from hematuria, anemia, dysuria, pyuria and pelvic pain. According to additional embodiments, a subject suspected if having BC indicates that the subject is at increased risk, relative to the general population, of developing bladder cancer. In certain embodiments, a subject has a personal and/or family medical history that might indicate the occurrences of a bladder cancer. In another embodiment, a subject has a susceptibility determined by genetic screening according to techniques known in the art. Particular embodiments are subjects who are at risk for developing bladder cancer, e.g. cigarette smokers or subjects exposed to other risk factors.

The 1973 WHO grading system for TCCs (papilloma, G1, G2 or G3) is most commonly used despite being superseded by the 2004 WHO grading (papillary neoplasm of low malignant potential (PNLMP), low grade and high grade papillary carcinoma.

According to the 1997 TNM system Bladder TCC is staged as follows: Ta-non-invasive papillary tumor; T1-invasive but not as far as the muscular bladder layer; T2-invasive into the muscular layer; T3-invasive beyond the muscle into the fat outside the bladder; T4-invasive into surrounding structures like the prostate, uterus or pelvic wall.

The term "invasive" as used herein refers to cells which have the ability to infiltrate surrounding tissue. The terms "non-invasive bladder cancer" or "non-invasive papillary tumor" as used herein refer to a very early cancer or a cancer that has not spread beyond the tissue of origin. According to particular embodiments, the non-invasive bladder cancer is selected from Ta or T1 stages. According to another embodiment, the non-invasive bladder cancer is at Ta stage. According to another embodiment, the non-invasive bladder cancer is at T1 stage.

The term "invasive cancer" refers to cancer that has spread beyond the layer of tissue in which it started into the normal surrounding tissues. Invasive cancers may or may not be metastatic. The term "muscle invasive bladder cancer" as used herein refers to a tumor that has spread into and/or beyond the muscular layer of the bladder. According to particular embodiments, the muscle invasive bladder cancer is selected from at least one stage selected from T2, T3 or T4 stages, as detailed hereinabove.

The following stages are used to classify the location, size, and spread of the cancer, according to the TNM (tumor, lymph node, and metastases) staging system: Stage 0: Cancer cells are found only on the inner lining of the bladder. Stage I: Cancer cells have proliferated to the layer beyond the inner lining of the urinary bladder but not to the muscles of the urinary bladder. Stage II: Cancer cells have proliferated to the muscles in the bladder wall but not to the fatty tissue that surrounds the urinary bladder. Stage III: Cancer cells have proliferated to the fatty tissue surrounding the urinary bladder and to the prostate gland, vagina, or uterus, but not to the lymph nodes or other organs. Stage IV: Cancer cells have proliferated to the lymph nodes, pelvic or abdominal wall, and/or other organs. Recurrent: Cancer has recurred in the urinary bladder or in another nearby organ after having been treated. According to particular embodiments, the non-invasive bladder cancer is selected from stages 0-stage I. According to particular embodiments, the muscle invasive bladder cancer is selected from stages II-IV.

Prostate Cancer

Adenocarcinoma of the prostate is the most common form of prostate cancer. Sarcoma of the prostate is rare, occurring primarily in children. Undifferentiated prostate cancer, squamous cell carcinoma, and ductal transitional carcinoma also occur infrequently. Prostatic intraepithelial neoplasia is considered a possible premalignant histologic change. Hormonal influences contribute to the course of adenocarcinoma but almost certainly not to other types of prostate cancer.

Prostate cancer usually progresses slowly and rarely causes symptoms until advanced. In advanced disease, symptoms of bladder outlet obstruction (e.g., straining, hesitancy, weak or intermittent urine stream, a sense of incomplete emptying, terminal dribbling) may appear. Bone pain may result from osteoblastic metastases to bone (commonly pelvis, ribs, vertebral bodies).

Grading, based on the resemblance of tumor architecture to normal glandular structure, helps define the aggressiveness of the tumor. Grading takes into account histologic heterogeneity in the tumor. The Gleason score is commonly used, wherein the most prevalent pattern and the next most prevalent pattern are each assigned a grade of 1 to 5, and the two grades are added to produce a total score. Most experts consider a score ≤6 to be well differentiated, 7 moderately differentiated, and 8 to 10 poorly differentiated. The lower the score, the less aggressive and invasive is the tumor and the better is the prognosis. Prostate cancer is also staged to define extent of the tumor (e.g. TRUS).

According to certain embodiments, a "subject suspected of having prostate cancer" indicates that the subject presents one or more symptoms or signs characteristic of prostate cancer. Non-limiting examples of symptom related to prostate cancer are urinary dysfunction, frequent urination, nocturia, hematuria, dysuria and bone pain. According to additional embodiments, a subject suspected of having prostate cancer indicates that the subject is at increased risk, relative to the general population, of developing prostate cancer. In certain embodiments, a subject has a personal and/or family medical history that might indicate the occurrences of a prostate cancer. In another embodiment, a subject has a susceptibility determined by genetic screening according to techniques known in the art. Particular embodiments are subjects who are at risk for developing prostate cancer, e.g. cigarette smokers or subjects exposed to other risk factors.

Antibodies, Immunoassays and Kits

The present invention provides in some embodiments diagnostic methods involving determining the urinary levels of the HSP and cytokine biomarkers of the invention. The methods of the invention may optionally and conveniently be affected using an immunoassay. The term "immunoassay" as used herein refers to a method of detecting or measuring antigens, in this case biomarkers of genitourinary cancer (e.g., BC and/or CaP), by using antibodies as reagents. The immunoassay is typically characterized by the use of specific binding properties of a particular antibody to isolate, target, and/or quantify the antigen.

Antibodies, or immunoglobulins, comprise two heavy chains linked together by disulfide bonds and two light chains, each light chain being linked to a respective heavy chain by disulfide bonds in a "Y" shaped configuration. Each heavy chain has at one end a variable domain (VH) followed by a number of constant domains (CH). Each light chain has a variable domain (VL) at one end and a constant domain (CL) at its other end, the light chain variable domain being aligned with the variable domain of the heavy chain and the light chain constant domain being aligned with the first constant domain of the heavy chain (CH1). The variable domains of each pair of light and heavy chains form the antigen binding site. The isotype of the heavy chain (gamma, alpha, delta, epsilon or mu) determines immunoglobulin class (IgG, IgA, IgD, IgE or IgM, respectively). The light chain is either of two isotypes (kappa, κ or lambda, λ) found in all antibody classes.

It should be understood that when the terms "antibody" or "antibodies" are used, this is intended to include intact antibodies, such as polyclonal antibodies or monoclonal antibodies (mAbs), as well as proteolytic fragments thereof such as the Fab or $F(ab')_2$ fragments. Further included within the scope of the invention (for example as immunoassay reagents, as detailed herein) are chimeric antibodies; recombinant and engineered antibodies, and fragments thereof.

Exemplary functional antibody fragments comprising whole or essentially whole variable regions of both light and heavy chains are defined as follows: (i) Fv, defined as a genetically engineered fragment consisting of the variable region of the light chain and the variable region of the heavy chain expressed as two chains; (ii) single-chain Fv ("scFv"), a genetically engineered single-chain molecule including the variable region of the light chain and the variable region of the heavy chain, linked by a suitable polypeptide linker; (iii) Fab, a fragment of an antibody molecule containing a monovalent antigen-binding portion of an antibody molecule, obtained by treating whole antibody with the enzyme papain to yield the intact light chain and the Fd fragment of the heavy chain, which consists of the variable and CH1 domains thereof; (iv) Fab', a fragment of an antibody molecule containing a monovalent antigen-binding portion of an antibody molecule, obtained by treating whole antibody with the enzyme pepsin, followed by reduction (two Fab' fragments are obtained per antibody molecule); and (v) F(ab')2, a fragment of an antibody molecule containing a monovalent antigen-binding portion of an antibody molecule, obtained by treating whole antibody with the enzyme pepsin (i.e., a dimer of Fab' fragments held together by two disulfide bonds).

Methods of generating monoclonal and polyclonal antibodies are well known in the art. Antibodies may be generated via any one of several known methods, which may employ induction of in vivo production of antibody molecules, screening of immunoglobulin libraries, or generation of monoclonal antibody molecules by continuous cell lines in culture. Antibody fragments may be obtained using methods well known in the art, including, but not limited to by proteolytic hydrolysis of the antibody or by expression in E. coli or mammalian cells (e.g., Chinese hamster ovary (CHO)) cell culture or other protein expression systems) of DNA encoding the fragment. Single-chain Fvs are prepared by constructing a structural gene comprising DNA sequences encoding the heavy chain variable and light chain variable domains connected by an oligonucleotide encoding a peptide linker. The structural gene is inserted into an expression vector, which is subsequently introduced into a host cell such as E. coli. The recombinant host cells synthesize a single polypeptide chain with a linker peptide bridging the two variable domains.

Antibodies for detecting the biomarkers of the invention may be purified or synthesized using methods well known in the art, e.g. by immunization with HSPs or cytokines antigens as described herein. HSPs and cytokines, that were identified as biomarkers according to the invention, have been described, e.g., in Lindquist et al., 1988; Kaufmann et al., 1990; Levine et at, 1991; Ciocca et al., 1993; Cappello et al., 2008; Fuller et al., 1994; Lebert et al., 2003; Lebret et cd., 2007; Kochac et al. 2004, Sheryka et al. 2003, Esuvaranathan et al. 1995, Cai et al. 2007, Loskog et al. 2007, Helmy et al. 2007, Cardillo and Ippoliti, 2006, Minty et al., 1993; McKenzie et al., 1993; Punnonen et al., 1993; Schmid-Grendelmeier et al., 2002; Brown et al., 1989; Terabe et al., 2000; Skinnider et al., 2001; Kapp et cd., 1999; Raz et al., 2001; and MalekZadeh et al., 2010 and may be purified, recombinantly synthesized or purchased as known in the art. According to certain particular embodiments, the biomarkers have the amino acid sequence as set forth in SEQ ID NO:1 to SEQ ID NO:9. Antibodies against the biomarkers of the invention are also commercially available, e.g. from StressMarq (CITY, Victoria, Canada), BioSource (Camarillo, Calif.), BioLegend (San Diego, Calif.), R&D Systems (Minneapolis, Minn.).

The term "antigen" as used herein is a molecule or a portion of a molecule capable of being bound by an antibody. The antigen is typically capable of inducing an animal to produce antibody capable of binding to an epitope of that antigen. An antigen may have one or more epitopes. The specific reaction (or specific binding) referred to above is meant to indicate that the antigen will react, in a highly selective manner, with its corresponding antibody and not with the multitude of other antibodies which may be evoked by other antigens.

Thus, the immune reactivity of the antibody to the antigen, i.e. its ability to specifically bind the antigen, may be used to determine the amount of the antigen in the sample. In another embodiment, detection of the capacity of an antibody to specifically bind an antigen may be performed by quantifying specific antigen-antibody complex formation.

In certain embodiments, the detection of the biomarker may be performed using an immunoassay such as an enzyme-linked immunosorbent assay (ELISA) testing kit. In such assays, for example, samples are typically incubated in the presence of an immobilized first specific binding agent (e.g. an antibody) capable of specifically binding the biomarker. Binding of the biomarker to said first specific binding agent may be measured using any one of a variety of known methods, such as using a labeled second specific binding agent capable of specifically binding the biomarker (at a different epitope) or the first specific binding agent.

Exemplary specific binding agents include e.g. monoclonal antibodies, polyclonal antibodies, and antibody fragments such as recombinant antibody fragments, single-chain antibodies (scFv) and the like.

In some embodiments, various conventional tags or labels may be used, such as a radioisotope, an enzyme, a chromophore or a fluorophore. A typical radioisotope is iodine$^{-125}$ or sulfur$^{-35}$. Typical enzymes for this purpose include horseradish peroxidase, horseradish galactosidase and alkaline phosphatase.

Alternately, other immunoassays may be used; such techniques are well known to the ordinarily skilled artisan and have been described in many standard immunology manuals and texts.

In some embodiments, the methods of the invention are suitable for automated or semi-automated analysis, and may enable clinical, medium or high-throughput screening of multiple samples. For example, automated ELISA systems such as Biotest's Quickstep® ELISA Processor, Maxmat Automated microwell ELISA analyzer (Maxmat S.A., France), or DSX™ Four-Plate System (Dynex Technologies) may conveniently be used.

Other suitable assays include for example flow cytometry assays (such as singleplex and multiplex bead-based Luminex® assays (Invitrogen).

Alternately, biomarkers may be captured on an antibody microarray. The antibody microarray comprises anti-biomarker antibodies, for example, a combination of anti-biomarker antibodies. In general, the sample (e.g., urine) obtained from the subject is placed on the active surface of a chip for a sufficient time to allow binding. Then, unbound molecules are washed from the surface using a suitable eluant, such as phosphate buffered saline. In general, the more stringent the eluant, the more tightly the biomarkers must be bound to be retained after the wash. The retained biomarkers now can be detected by appropriate means.

Additional exemplary assays may be based on dipstick technology, as demonstrated, for example, in U.S. Pat. Nos. 4,632,901, 4,313,734 and 4,786,589 5,656,448 and EP 0125118. For example, U.S. Pat. No. 4,632,901, discloses a flow-through type immunoassay device comprising antibody (specific to a target antigen analyte) bound to a porous membrane or filter to which is added a liquid sample. As the liquid flows through the membrane, target analyte binds to the antibody. The addition of sample is followed by addition of labeled antibody. The visual detection of labeled antibody provides an indication of the presence of target antigen analyte in the sample. EP 0125118 discloses a sandwich type dipstick immunoassay in which immunochemical components such as antibodies are bound to a solid phase. The assay device is "dipped" for incubation into a sample suspected of containing unknown antigen analyte. Enzyme-labeled antibody is then added, either simultaneously or after an incubation period. The device next is washed and then inserted into a second solution containing a substrate for the enzyme. The enzyme-label, if present, interacts with the substrate, causing the formation of colored products which either deposit as a precipitate onto the solid phase or produce a visible color change in the substrate solution.

For example, the method may be performed by the steps comprising:
a) collecting a urine sample from the subject;
b) contacting the sample, under conditions such that a specific antigen-antibody complex may be formed, with at least one antibody, said antibody being directed to a marker antigen of the invention (e.g., IL-13, IL-10, IL-8, HSP60, HSP70 or HSP90);
c) quantifying the amount of antigen-antibody complex formed, wherein said amount is indicative of the amount of said marker in said sample.

An antibody "directed to" an antigen, as used herein is an antibody which is capable of specifically binding the antigen. The term "specifically bind" as used herein means that the binding of an antibody to an antigen is not competitively inhibited by the presence of non-related molecules. Antibodies directed to IL-6, IL-8, IL-10, IL-13, TGF-β, HSP60, HSP70 and HSP90 may be prepared using well known methods, for example as detailed hereinabove. Alternatively, antibodies, or ELISA kits for determining the presence of these antigens, may be purchased from a variety of sources. For example, antibodies for detection of HSP60 and HSP90 are commercially available from Santa Cruz Biotechnology (Santa Cruz, Calif.), antibodies for detection of HSP70 are commercially available from StressMarq (CITY, Victoria, Canada), and ELISA antibody sets for detection of IL-6, IL-10 and IL-8, sets are commercially available from BioLegend (San Diego, Calif.) and IL-13 and TGFβ ELISA, sets are commercially available from R&D Systems (Minneapolis, Minn.).

Optionally, steps b) and c) may be repeated for one or more additional marker antigens of the invention as detailed herein.

In various embodiments, a significant elevation in the level of marker compared to control is indicative of the presence of bladder cancer (or, in other embodiments, of invasive bladder cancer), as detailed herein. In the methods of the invention, a "significant elevation" in the level (or amount) of a urinary marker refers, in different embodiments, to a statistically significant elevation, or in other embodiments to a significant elevation as recognized by a skilled artisan. For example, without limitation, the present invention demonstrates that an increase of either 10 ng/ml of HSP60 or 10 pg/ml of IL-13 is associated with more than ten times the chance of BC. In some embodiments, a statistically significant difference between the level of the antigen in the sample obtained from the subject compared to a normal level of the antigen (e.g., the level in a healthy control population) is an indication that the subject is afflicted with bladder cancer. In other embodiments, a statistically significant difference between the level of the antigen in the sample obtained from the subject compared to the level of the antigen in a subject afflicted with non-invasive cancer (e.g., the level in a control population of non-muscle invasive BC patients) is an indication that the subject is afflicted with invasive bladder cancer.

The urine sample is obtained or collected from the subject as is known in the art. In one embodiment, the urine sample is a voided urine sample. In certain other embodiments, the sample is collected from the subject without a preceding step of bladder scraping or washing. In another embodiment, the method further comprises the step of freezing the urine sample of step a) and thawing the sample prior to step b). Conveniently, urine samples may be kept at −20° C. until the analysis is performed.

In various embodiments, the method of the present invention further comprises diluting the urine sample before determining the level of the biomarker, in particular IL-13, in the sample. In one embodiment, the sample is diluted 1:2, for instance, using PBS. In another embodiment, the sample is diluted 1:4, 1:6, 1:8, 1:10, 1:15 or 1:20. Preferably, the samples are diluted 1:8. Each possibility represents a separate embodiment of the present invention.

In another embodiment, the urine sample undergoes filtration. In a preferable embodiment, the sample undergoes ultra-filtration using, for instance, a MILLIPORE Amicon Ultra. As is known in the art, ultra-filtration relates to a variety of membrane filtration in which hydrostatic pressure forces a liquid against a semipermeable membrane. The cut-off of the membrane may be selected from 3KD, 10KD, 30KD or more. Preferably, the cut-off used in said filtration is 3KD. In another embodiment, the sample is reconstituted (e.g. with PBS). In another embodiment, following reconstitution, the urine sample is diluted in the range of times 2-times 10. In another embodiment, the urine sample is diluted in the range of times 2-times 8. In another embodiment, the urine sample is diluted in the range of times 2-times 6. In another embodiment, the urine sample is diluted in the range of times 2-times 4. In another embodiment, the urine sample is diluted times 3. Each possibility represents a separate embodiment of the present invention.

In some embodiments, the subject has not received an anti-cancer treatment (e.g. local or systemic chemotherapy)

prior to (or adjacent to) collecting the urine sample. In one embodiment, the subject has not received an intravesical therapy (e.g. BCG or mitomycin treatment). In another embodiment, the subject has not received an immunomodulating therapy (e.g. anti-inflammatory drugs). In yet other embodiments, the subject has received an anti-cancer treatment prior to (or adjacent to) collecting the urine sample.

The methods of the invention may, in various embodiments, be used as a single diagnostic assay, or in combination with other diagnostic methods such as cytology or cytoscopy, as known in the art.

Diagnostic Kits

According to further aspects the present invention provides kits suitable for use in methods of diagnosing genitourinary cancer such as bladder cancer or prostate cancer, in a subject. Thus, in another embodiment, there is provided a diagnostic kit comprising i) means for collecting a urine sample from a subject and ii) means for determining the level of at least one marker of the invention in the sample.

In other embodiments, the kit may contain reagents, detectable labels and/or containers which may be used for measuring specific binding of antibodies to the marker antigens of the invention. In other embodiments, the kit may further comprise negative and/or positive control samples. For example, control samples may contain a sample from at least one healthy individual (negative control) or at least one individual identified with bladder cancer (positive control), a panel of control samples from a set of healthy individuals or diseased individuals, or a stored set of data corresponding to control individuals. In another embodiment, the kit may contain control samples obtained from patients having superficial or invasive bladder tumors. Optionally, the kits may further comprise means for preparing or storing the sample before measuring the antigen levels.

According to another embodiment, the invention provides a kit comprising i) means for determining the level of at least one marker of the invention in a urine sample and ii) at least one control value or control sample, as described herein. In various embodiments, the control value or control sample may be a negative control corresponding to a healthy subject, e.g. a value obtained from a healthy control individual not diagnosed with a disease, a panel of control values from a set of healthy individuals, and a stored set of data corresponding to control individuals that are not afflicted with bladder cancer, a positive control corresponding to a subject having low-grade bladder cancer, e.g. a value obtained from an individual having non-invasive bladder cancer, a panel of control values obtained from individuals having non-invasive bladder cancer, and a stored set of data corresponding to control individuals, or a positive control corresponding to a subject having invasive bladder cancer, e.g. a value obtained from an individual having invasive bladder cancer, a panel of control values obtained from individuals having invasive bladder cancer, and a stored set of data corresponding to control individuals having muscle-invasive cancer.

According to another embodiment, the invention provides a kit comprising i) means for determining the level of at least one marker of the invention in a urine sample and ii) instructions for performing the necessary steps, for diagnosing genitourinary cancer (e.g., BC or CaP).

Diagnostic Use

According to another aspect, the present invention provides use of means for detecting at least one urinary biomarker selected from the group consisting of IL-13, IL-10, HSP60, HSP70 and HSP90 for the preparation of a diagnostic composition for assessing (or determining) the presence or absence of bladder cancer in a subject. In one embodiment, a significant elevation in the level of the at least one urinary biomarker compared to a control value corresponding to a healthy individual indicates that said subject is afflicted with bladder cancer. In one embodiment, the subject is suspected of having bladder cancer. In one embodiment, the biomarkers are selected from the group consisting of IL-13, IL-10 and HSP60. In yet another embodiment, the biomarkers are selected from the group consisting of IL-13 and HSP60. In another particular embodiment, the biomarker is IL-13. Each possibility is a separate embodiment of the invention.

In another embodiment, the present invention provides use of means for detecting a plurality of urinary biomarkers selected from the group consisting of IL-13, IL-10, HSP60, HSP70 and HSP90 for the preparation of a diagnostic composition for assessing (or determining) the presence or absence of bladder cancer in a subject. For example, a significant elevation in the level of the at least one two, three, four or more of the biomarkers in a urine sample obtained from the subject, compared to a control value corresponding to a healthy individual, indicates that said subject is afflicted with bladder cancer. Optionally and preferably, the levels of at least one heat shock protein and at least one cytokine are measured. In a particular embodiment, the biomarkers are IL-13 and HSP60.

In another aspect, the invention provides use means for detecting of at least one urinary biomarker selected from the group consisting of HSP60, HSP70 and HSP90, for the preparation of a diagnostic composition for assessing (or determining) the presence or absence of muscle invasive bladder cancer in a subject, wherein a significant elevation in the level of the at least one biomarker compared to a control value indicates that said subject is afflicted with muscle invasive bladder cancer.

According to another aspect, the present invention provides use of means for detecting at least one urinary biomarker selected from the group consisting of IL-13 and IL-1β for the preparation of a diagnostic composition for assessing (or determining) the presence or absence of prostate cancer in a subject, wherein a significant elevation in the level of the at least one biomarker compared to a control value corresponding to a healthy individual indicates that said subject is afflicted with prostate cancer. In one embodiment, the subject is suspected of having prostate cancer.

In another embodiment, the present invention provides use of means for detecting IL-13 for the preparation of a diagnostic composition for diagnosing a genitourinary cancer in a subject in need thereof (e.g., suspected of having genitourinary cancer), wherein a significant elevation in the level of IL-13, in a urine sample obtained from the subject, compared to a control value corresponding to a healthy individual indicates that said subject is afflicted with genitourinary cancer. According to one embodiment, the present invention provides means for detecting IL-13 and at least one biomarker selected from the group consisting of HSP60, HSP70, HSP90, IL-10, IL-8 and IL-1β for diagnosing a genitourinary cancer in said subject, wherein:

(i) a significant elevation in the level of IL-13 and at least one biomarker selected from the group consisting of HSP60, HSP70, HSP90, IL-10 and IL-8 compared to a control value corresponding to a healthy individual, indicates that said subject is afflicted with bladder cancer; and (ii) a significant elevation in the level of IL-13 and IL-1β compared to a control value corresponding to a healthy individual indicates that said subject is afflicted with prostate cancer.

In another embodiment, the method comprises determining the level of IL-13, HSP60, HSP70 and HSP90 in a urine sample obtained from the subject, wherein:

i. a significant elevation in the level of IL-13 in the sample compared to a negative control value corresponding to a healthy individual indicates that said subject is afflicted with bladder cancer; and in a subject thus diagnosed as having bladder cancer ii. a significant elevation in the level of HSP60, HSP70 and HSP90 in the sample compared to a positive control value corresponding to an individual having non-invasive bladder cancer indicates that said subject is afflicted with invasive bladder cancer, and a level of HSP60, HSP70 and HSP90 which is not significantly elevated compared to the positive control value indicates that the subject has non-invasive bladder cancer.

The following examples are presented in order to more fully illustrate some embodiments of the invention. They should, in no way be construed, however, as limiting the broad scope of the invention.

EXAMPLES

A. Human Subjects and Methods—BC Diagnosis

Subjects

The study was approved by the Rabin Medical Center Institutional Review Board. Banked serum and urine samples were obtained from 106 consecutive patients—88 of whom were undergoing cystoscopy and biopsy for suspected bladder cancer—and from 18 age-matched healthy controls. The serum and urine specimens were taken before cystoscopy, immediately frozen and stored at −20° C. The healthy controls were assigned to Group 1. The biopsied subjects were assigned to the following categories after transurethral resection (TUR) of suspected lesions: Group 2-hematuria with no evidence of malignancy (n=20); Group 3—non-muscle invasive BC, stage=CIS, Ta or T1 (non-MI-BC; n=50); Group 4—muscle-invasive BC, stage ≥T2 (MI-BC; n=18). One patient with a positive urine culture indicating bacterial cystitis was excluded.

Table 1 presents the clinical and pathological characteristics of the subjects. There were no significant differences between the various groups in age, smoking status, renal function, or type II diabetes. TUR specimens were processed and analyzed by a single genitourinary pathologist according to a standardized protocol. Pathological staging was reported in accordance with the 1997 Tumor-Node-Metastasis Classification, and assigned grade according to the WHO classification.

TABLE 1

Subject characteristics

| | Muscle invasive BC n = 18 | Non-Muscle invasive BC n = 50 | Hematuria No BC n = 20 | Healthy Control n = 18 | p value |
|---|---|---|---|---|---|
| Age (mean ± SD) | 71.5 ± 10.13 | 69.3 ± 10.21 | 66 ± 15.2 | 65.9 ± 6.7 | N.S |
| Gender (%) | M = 80% F = 20% | M = 86% F = 14% | M = 89% F = 11% | M = 90% F = 10% | N.S |
| Smoking (%) | 53% | 44% | 55% | 55% | N.S |
| Creatinine | 1.2 ± 0.16 | 1.02 ± 0.3 | 1.3 ± 0.22 | 0.9 ± 0.11 | N.S |
| Diabetes (%) | 53% | 32% | 50% | 40% | N.S |

Reagents

Human HSP 60 was prepared as described (Quintana et al., 2000). HSP 70 and HSP90 were purchased from StressGen Biotechnologies (Victoria, BC, Canada). Antibodies for detection of HSP60 and HSP90 were purchased from Santa Cruz Biotechnology (Santa Cruz, Calif.). Antibody for detection of HSP70 was purchased from StressMarq (CITY, Victoria, Canada). ELISA antibody sets for detection of IFNγ, TNFα, IL-1β and IL-2 were purchased from BioSource (Camarillo, Calif.). For IL-6, IL-10 and IL-8, sets were purchased from BioLegend (San Diego, Calif.). For IL-4, 13 and TGFβ, sets were purchased from R&D Systems (Minneapolis, Minn.).

HSP Measurements

A direct enzyme-linked immunosorbent assay (ELISA) was used to quantify HSP concentrations in urine and serum. Assays were done in triplicate according to the manufacturer's instructions. Minimal detection concentrations were 20 ng/ml for HSP60 and HSP 70, and 5 ng/ml for HSP 90.

Cytokine Urine Measurements

Sandwich ELISA was used to quantify cytokine concentrations in urine. The assays were done in triplicates according to the manufacturer's instructions. The minimal detection concentration was 30 pg/ml for each of the cytokines. Patients who had received treatment with BCG or mitomycin were excluded, because these intravesical treatments can affect urinary cytokine levels. Cytokine measurements were performed in 72 subjects.

These 72 subjects were stratified according to the pathologic findings as follows: Group 1—healthy controls (n=18); Group 2—hematuria with no evidence of malignancy (n=13); Group 3—non-muscle invasive urothelial carcinoma (non-MI-BC; n=26); Group 4—muscle-invasive transitional cell carcinoma, stage ≥T2 (MI-BC; n=15).

Statistical Analysis

Univariate analysis was performed to assess the differences between HSP and cytokine concentrations in the four groups, using one way ANOVA. When the ANOVA test demonstrated a significant value, post-hoc LSD (least significant difference) analysis was used to determine statistically significant differences between the groups. To assess the association of each measurement with BC, the test subjects were divided into two groups: subjects with no bladder cancer (n=32) and patients with BC (n=40).

The National Cancer Institute recommends evaluating the performance of potential markers for cancer detection using receiver operating curves (ROC) (Pepe et al., 2001). Therefore, ROC were used to calculate the area under the curve and the 95% confidence interval (AUC±95% CI) for association with the presence of BC in general and for an association with the stage of disease: MI-BC and non-MI-BC).

A multivariate stepwise binary logistic regression to produce a predictive model utilizing a minimum number of variables was applied to discriminate between BC and controls. Samples that included urinary HSP and cytokine measurements were analyzed (n=72). Subjects were divided into two groups: controls (n=31) and patients with BC (n=41). The model included urinary HSP and cytokine concentrations and age. The odds ratio (OR), the 95% CI of statistically significant markers, and the AUC±95% CI of the entire model were calculated. The same model was applied for bladder cancer stage (MI-BC vs. non-MI-BC). Statistical analyses were carried out using SPSS statistical software version 12.0 (SPSS Inc, Chicago, Ill.); $p<0.05$ was considered significant.

IL-13 Detection in an Independent Group

An independent group of urine samples obtained from BC patients and controls was studied to evaluate IL-13 as a urinary biomarker. In these additional urine samples, it was discovered that the test was encumbered by the presence of inhibitors of IL-13 detection. To overcome this problem, different urine concentrations were spiked with pure IL-13 and it was discovered that the inhibitors could be diluted out at 1:8 (Urine: PBS). To inactivate these inhibitory factors and thus restore the ability to detect the IL-13, the urine was prepared in the following manner: first, the urine was filtered using MILLIPORE Amicon Ultra with Cut off of 3 KD (Cat number: UFC500324). The urine volume was then reconstituted with PBS, and subsequently diluted times 3. The urine was then assayed for IL-13 by ELISA (Detection limit: 100 pg/ml-3 pg/ml). The kits were purchased from Orgenium Laboratories, Finland. The urine levels of IL-13 were analyzed using this approach in groups composed of 20 controls (no BC) and 20 patients with BC.

Example 1

Urinary Concentrations of Heat Shock Proteins

Figure 1B:
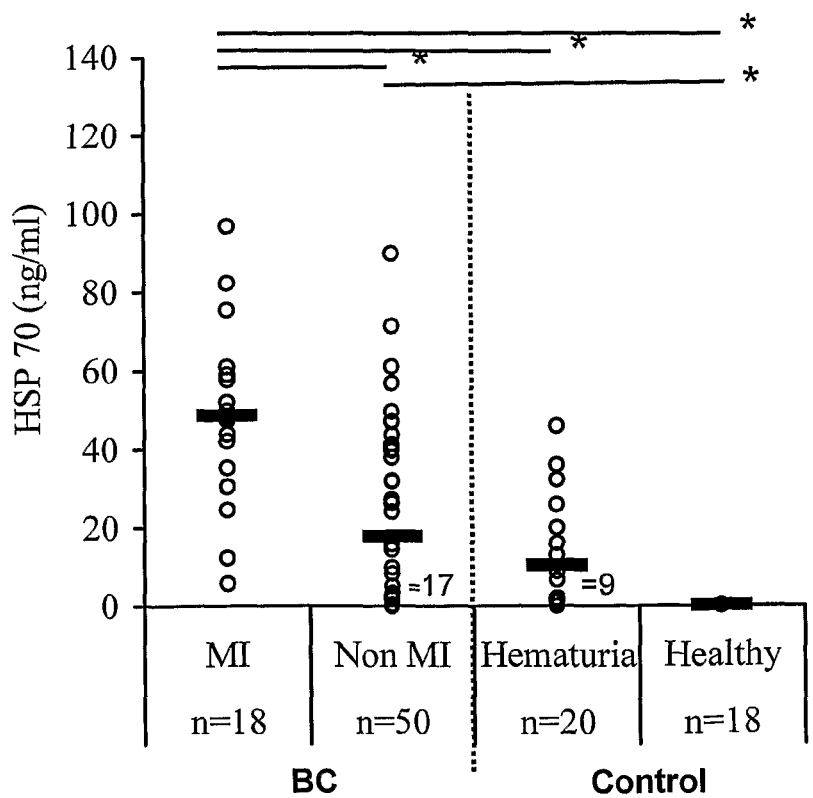
Figure 1C:
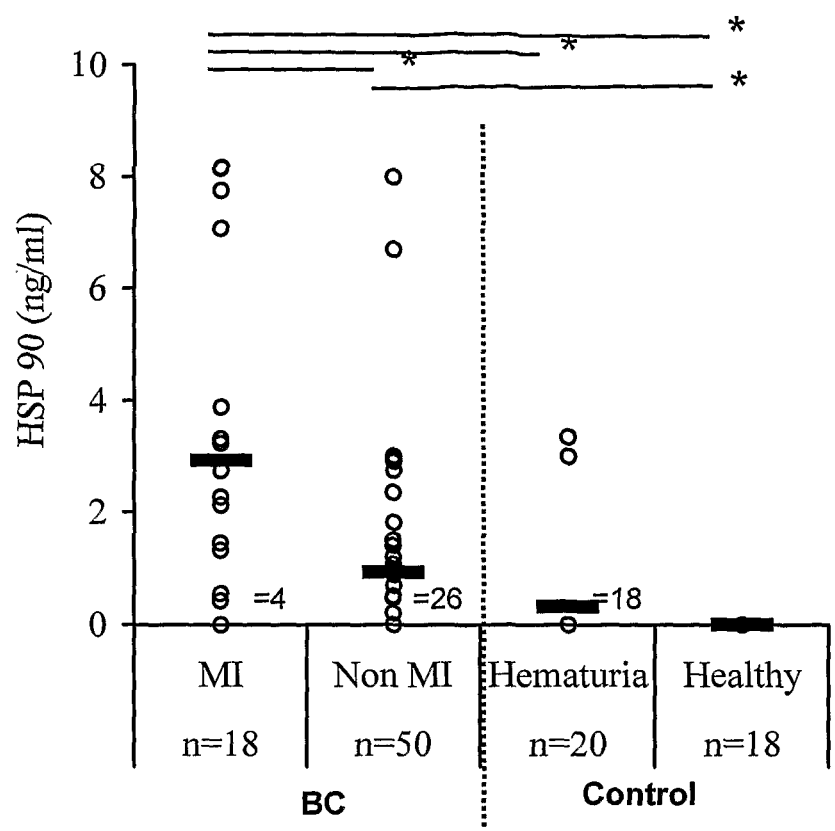
Figure 2A:
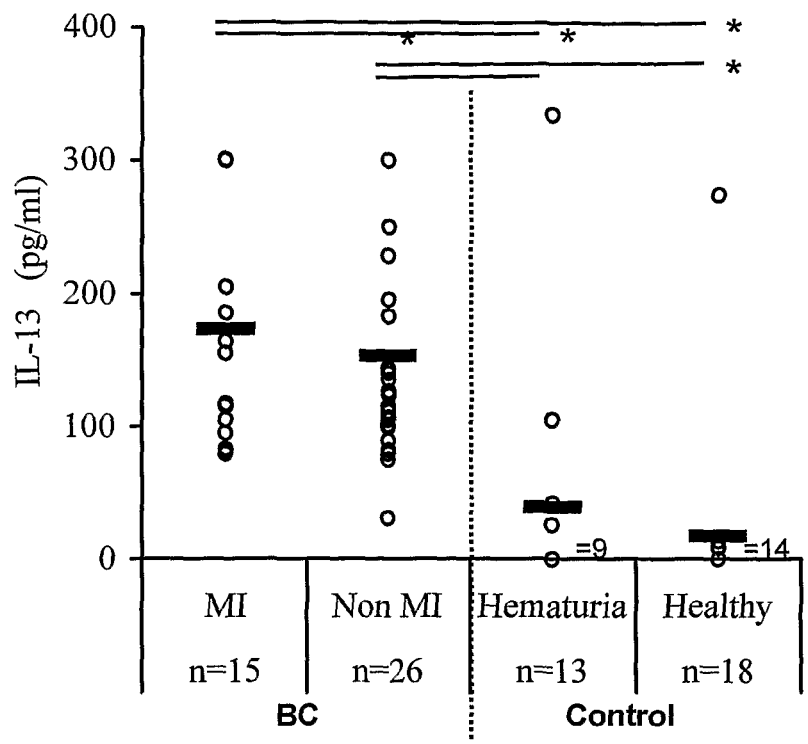
FIG. 2. Urinary concentrations of cytokines IL-6 (a), IL-8 (b), IL-10 (c), IL-13 (d) and TGF-β (e). Urine was assayed by ELISA for the presence of IL-6 (a), IL-8 (b), IL-10 (c), IL-13 (d) and TGF-β (e). The results are presented by a scatter plot—each dot represents one patient. Only one dot is presented when urinary concentrations overlap, the number of overlapping patients is indicated. *, $p<0.05$ by one-way ANOVA followed by least significant difference (LSD) post-hoc test.
Figure 2B:
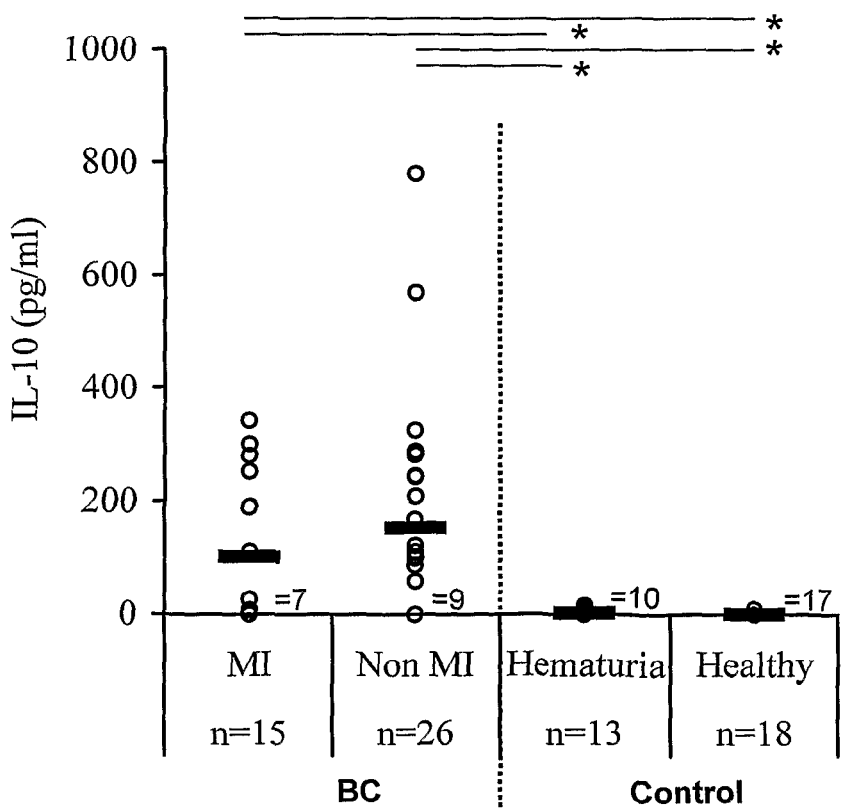
Figure 2C:
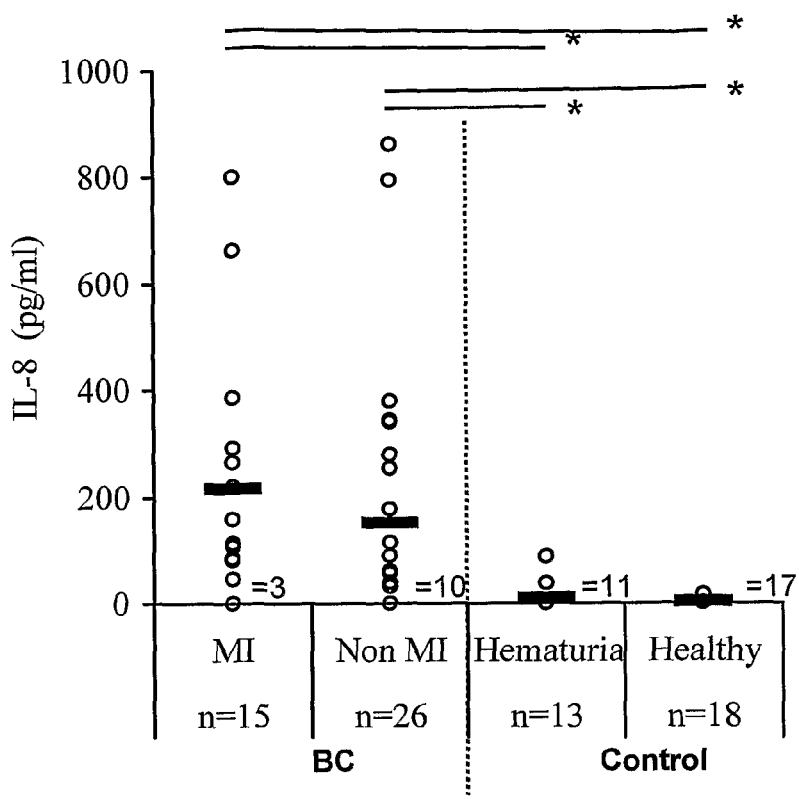
Figure 2D:
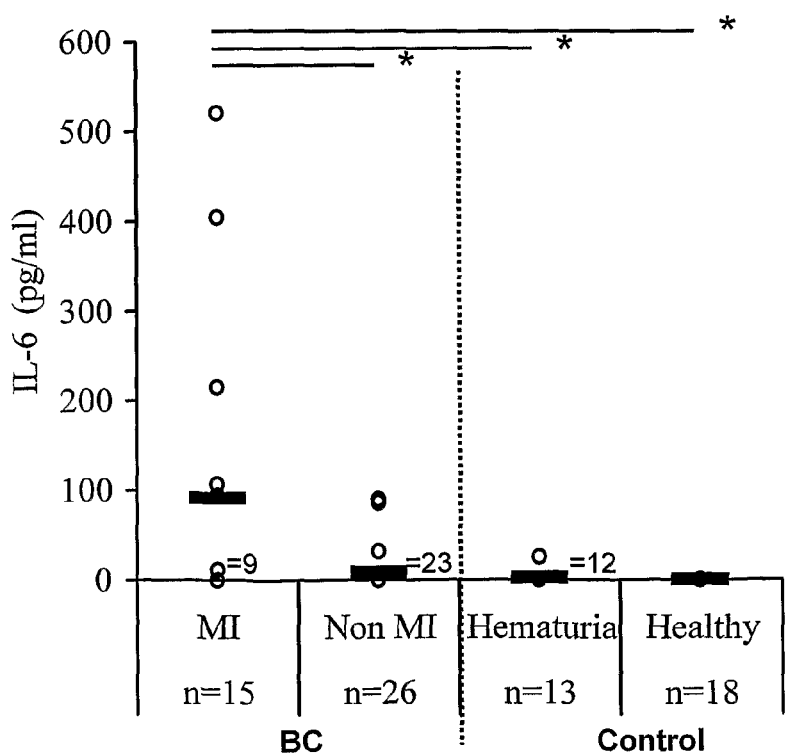
Figure 2E:
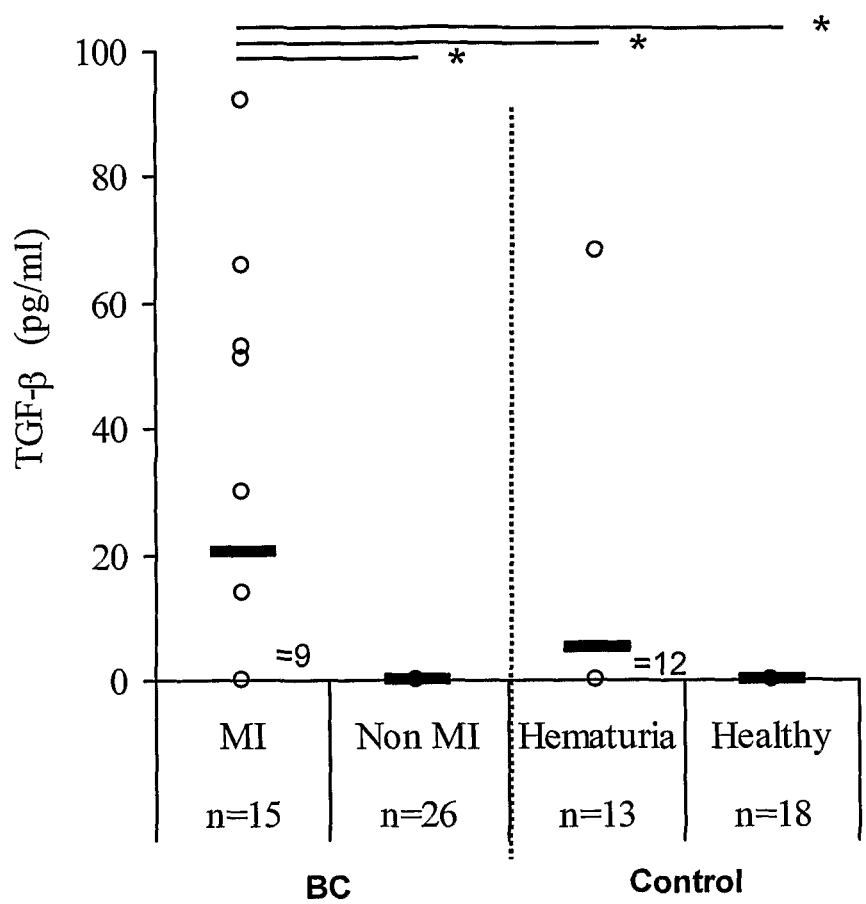

FIG. 1A-C depicts the distribution of HSP 60, HSP70 and HSP90 urinary concentrations classified by the different subject groups. Urine concentrations of HSP60 (FIG. 1A, Table 2) were significantly elevated in MI-BC compared to the other groups. The HSP60 concentration distinguished between healthy controls and BC patients, but did not separate subjects with hematuria from those with non-MI-BC. Urinary levels of HSP 70 (FIG. 1B, Table 2) showed similar concentration patterns between the subject groups. However, urinary concentrations of HSP70 exhibited a wider distribution than did HSP60. Urinary HSP90 (FIG. 1C, Table 2) concentrations were considerably lower than HSP60 and HSP70, but the patterns among the subject groups were similar. HSP could not be detected in the sera of BC patients or healthy controls.

TABLE 2

Urinary HSP and cytokine concentrations (mean ± SD)

|  | MI-BC | Non-MI-BC | Hematuria | Healthy |
|---|---|---|---|---|
| HSP 60 ng/ml | 52.4 ± 7.9 | 26 ± 1.8 | 24.6 ± 0.6 | 0 ± 0 |
| HSP 70 ng/ml | 47.5 ± 8.2 | 18.6 ± 4.6 | 8.3 ± 2.6 | 0 ± 0 |
| HSP 90 ng/ml | 2.6 ± 0.71 | 1.8 ± 0.5 | 0.5 ± 0.3 | 0 ± 0 |
| IL-6 pg/ml | 90 ± 42.5 | 8 ± 4.7 | 1.2 ± 2 | 0 ± 0 |
| IL-8 pg/ml | 214.3 ± 62.5 | 151 ± 47 | 9.6 ± 7.1 | 0.9 ± 0.5 |
| IL-10 pg/ml | 100.5 ± 34 | 152 ± 36 | 2 ± 1.1 | 2.1 ± 0.5 |
| IL-13 pg/ml | 172 ± 22 | 152 ± 15 | 39 ± 25 | 16 ± 15 |
| TGF-β pg/ml | 20.4 ± 7.8 | 0 ± 0 | 5.1 ± 5.2 | 0 ± 0 |

Example 2

Urinary Cytokine Concentrations

The concentrations of the various cytokines in the urine were examined. IFNγ, TNFα, IL-1β, IL-2, IL-4 and IL-5 were not detected; but IL-6, IL-8, IL-10, IL-13 and TGF-β were detected (FIG. 2 A-E). Urinary concentrations of IL-8, IL-10 and IL-13 (FIG. 2A-C, Table 2) were significantly elevated in BC patients compared to controls. However they did not distinguish between MI-BC and non-MI-BC. In contrast to IL-8 and IL-10, all of the BC patients manifested detectable levels of IL-13.

Urinary levels of IL-6 and TGF-β (FIGS. 2D and E, Table 2) were significantly elevated in MI-BC compared to the other groups. Six of 15 patients with MI-BC expressed detectable amounts of IL-6 or TGF-β. A single control subject with hematuria manifested elevated IL-6 and a different hematuria subject manifested elevated TGF-β.

Example 3

HSP Molecules and Cytokines are Biomarkers for BC

Figure 3A:
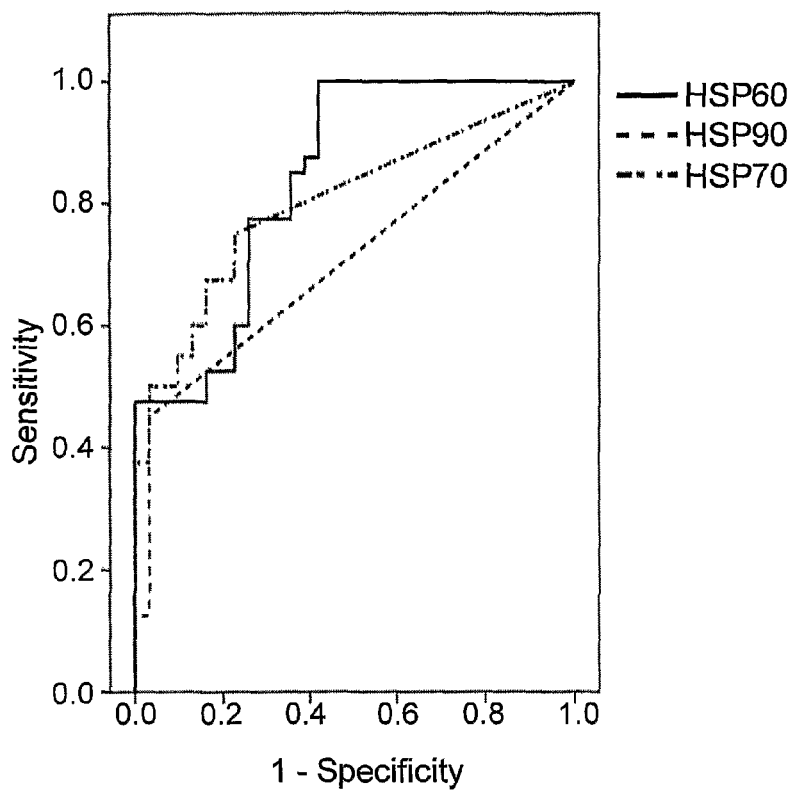
FIG. 3. ROC curve of HSPs (a) and cytokines (b) in BC detection
Figure 3B:
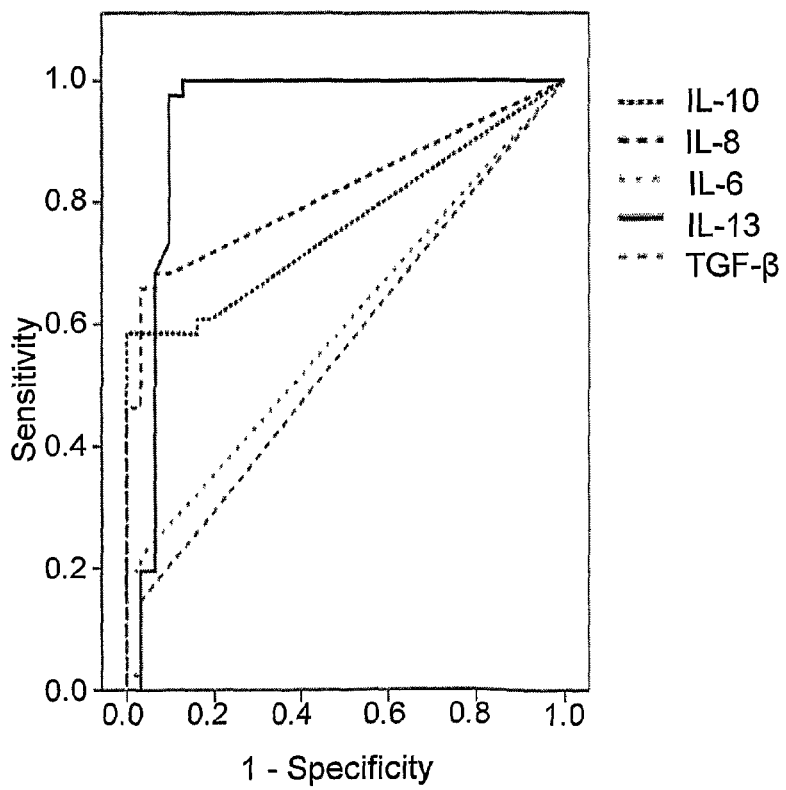

Next, a ROC analysis was used to determine the performance of the various HSP and cytokines as markers for BC according to the recommendation of the National Cancer Institute for early-phase biomarker development. FIGS. 3A, and 3B, and table 3 demonstrate the ROC and the AUC of the HSP and cytokine assays for BC. IL-13 appeared to be the most prominent marker for BC (AUC 0.93; 95% CI 0.85-0.99). However, except for TGF-β and IL-6, the other positive markers exhibited an AUC of 0.70 or greater for BC.

TABLE 3

Area under the curve ±95% CI of the ROC for BC

|  | AUC | 95% CI | p |
|---|---|---|---|
| HSP 60 | 0.84 | 0.75-0.93 | <0.001 |
| HSP 70 | 0.80 | 0.70-0.90 | <0.001 |
| HSP 90 | 0.70 | 0.58-0.82 | 0.003 |
| IL-6 | 0.56 | 0.47-0.73 | 0.15 |
| IL-8 | 0.81 | 0.71-0.91 | <0.001 |
| IL-10 | 0.77 | 0.66-0.88 | <0.001 |
| IL-13 | 0.93 | 0.85-0.99 | <0.001 |
| TGF-β | 0.557 | 0.42-0.69 | 0.41 |

A multivariate stepwise binary logistic regression analysis (Table 5) that adjusted for age and included all HSPs and cytokines was used to identify the minimal number of combined markers associated with BC. This model highlighted HSP60 and IL-13: HSP 60 (Odds Ratio 1.206; 95% CI 1.041-1.397; p=0.003) and IL-13 (Odds Ratio 1.020; 95% CI 1.007-1.033; p=0.012). The AUC±95% CI of the ROC of the multivariate model was 0.95; 95% CI 0.87-0.98.

Example 4

Elevated HSP and Cytokine Measurements are Associated with MI-BC

Figure 4A:
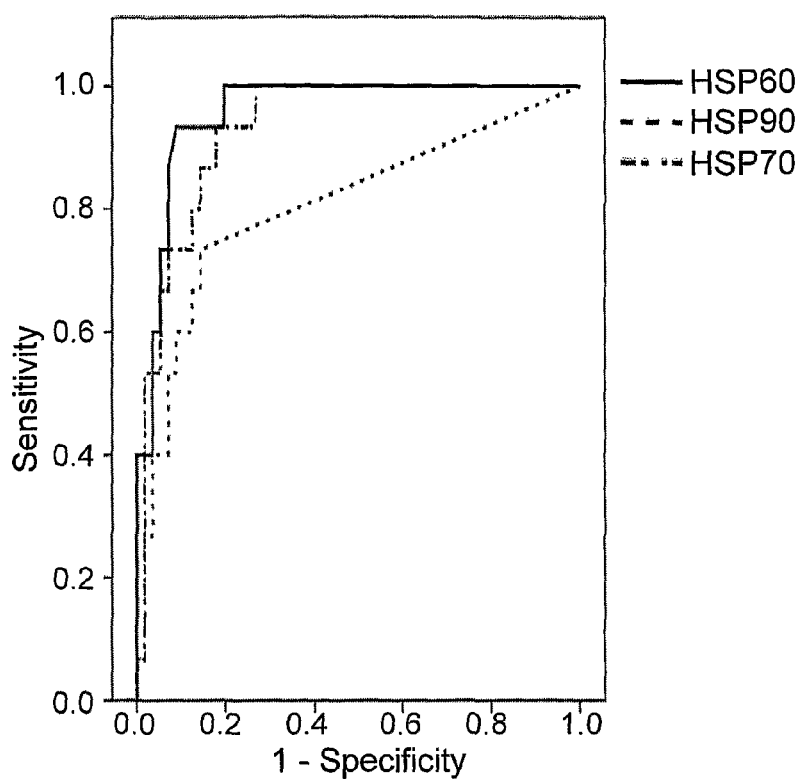
FIG. 4. ROC curve of HSPs (a) and cytokines (b) for BC stage prediction
Figure 4B:
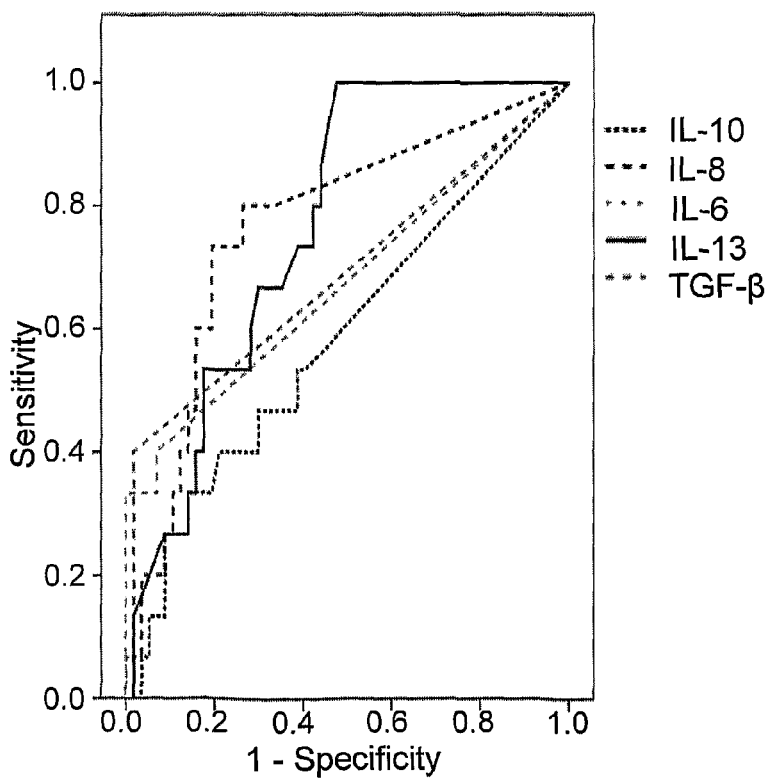

The association of these markers with the stage of BC was analyzed next. FIG. 4 A B, and Table 4 demonstrate the association between the stage of BC and urinary HSP and cytokines levels. HSP60 (AUC 0.95; 95% CI 0.91-0.99) showed the closest association with BC stage in this study. But an AUC of greater than 0.70 was demonstrated by HSP70, HSP90, IL-8 and IL-13.

TABLE 4

Area under the curve ±95% CI of the ROC for MI-BC

|  | AUC | 95% CI | p |
|---|---|---|---|
| HSP 60 | 0.95 | 0.91-0.99 | <0.001 |
| HSP 70 | 0.93 | 0.90-0.99 | <0.001 |
| HSP 90 | 0.80 | 0.66-0.92 | <0.001 |
| IL-6 | 0.67 | 0.5-0.85 | 0.04 |
| IL-8 | 0.76 | 0.62-0.90 | 0.002 |
| IL-10 | 0.58 | 0.41-0.74 | 0.32 |
| IL-13 | 0.77 | 0.66-0.88 | 0.001 |
| TGF-β | 0.67 | 0.51-0.86 | 0.026 |

To identify the minimal number of combined markers associated with MI-BC, a multivariate stepwise binary logistic regression analysis (Table 5) that adjusted for age and included HSPs and cytokines was used. This model highlighted HSP60, HSP70 and HSP90: HSP 60 (Odds Ratio 1.093; 95% 1.013-1.179; p=0.022), HSP70 (Odds Ratio 1.092; 95% CI 1.09-1.128) and HSP90 (Odds Ratio 2.404; 95% CI 1.231-4.694; p=0.01). The AUC±95% CI of the ROC of the model was 0.96; 95% CI was 0.89-0.98.

TABLE 5

Stepwise binary logistic regression to detect BC and MI-BC

| | Marker | OR | 95% CI | p |
|---|---|---|---|---|
| BC | IL-13 | 1.02 | 1.007-1.033 | 0.012 |
| | HSP 60 | 1.21 | 1.041-1.397 | 0.003 |
| MI-BC | HSP 60 | 1.09 | 1.013-1.179 | 0.022 |
| | HSP 70 | 1.09 | 1.09-1.128 | 0.004 |
| | HSP 90 | 2.40 | 1.23-4.694 | 0.01 |

Example 5

Detection of IL-13 as a Urinary Biomarker of BC

Figure 7:
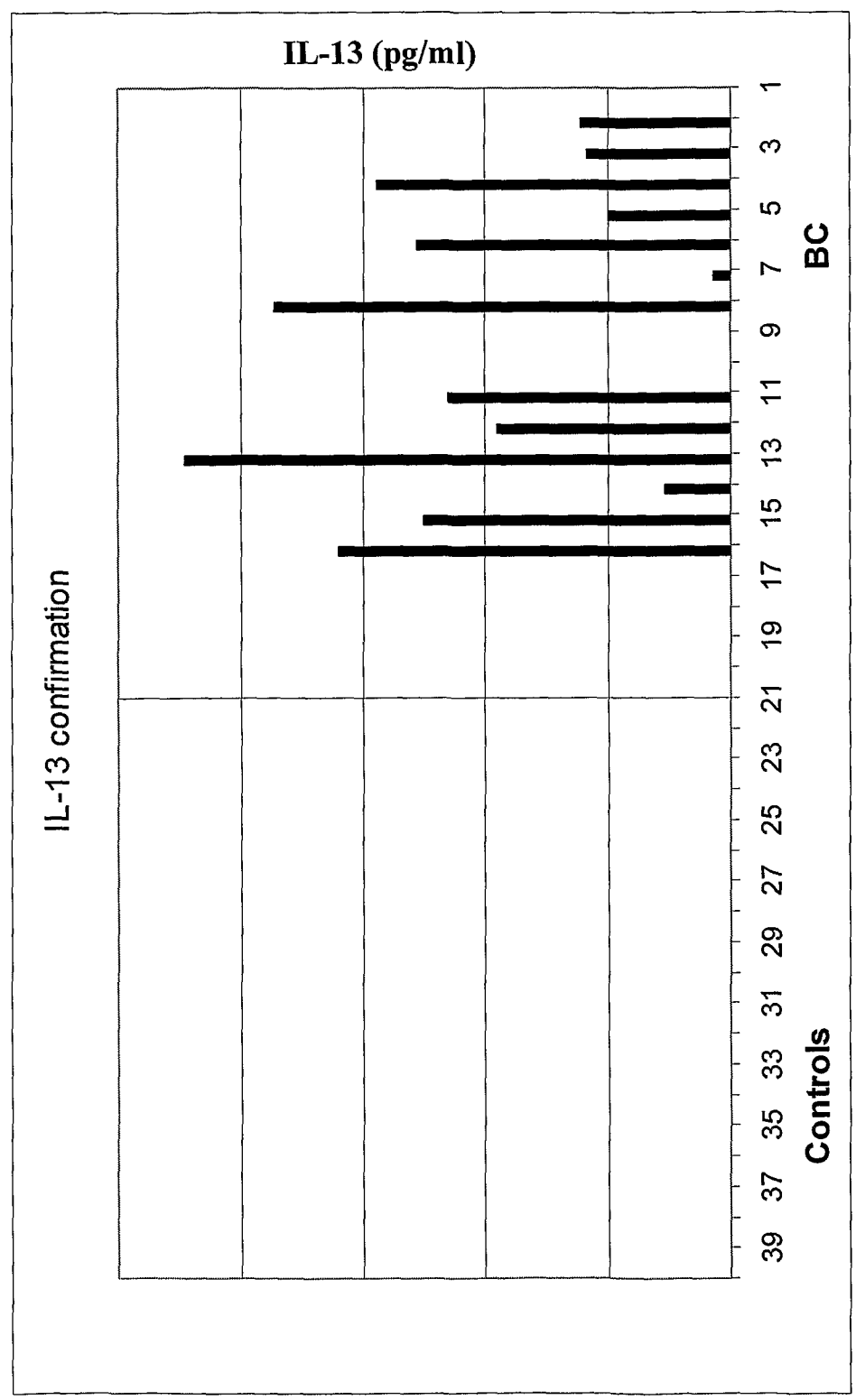
FIG. 7. Detection of IL-13 as a urinary biomarker of BC. Urine was assayed by ELISA for the presence of IL-13 as described. The results are presented in a bar chart—each bar represent urinary IL-13 concentrations of one patient.

Since this is the first report of urinary levels of IL-13 in BC, experiments were performed to confirm these findings in independent groups of subjects. FIG. 7 depicts the urinary concentrations of IL-13 in the confirmation group. As demonstrated, 13 of 20 (65%) BC patients had high urinary IL-13 levels and no subject in the control group was positive for detectable IL-13 (p<0.001). Therefore IL-13 was identified and confirmed as a robust urinary biomarker of BC.

B. Human Subjects and Methods—CaP Diagnosis

Subjects

The study was approved by the Rabin Medical Center Institutional Review Board. Banked urine samples were obtained from 36 consecutive patients, all were referred for a prostate either due to an elevated PSA (PSA cutoff was 3 ng/ml; n=27) or abnormal digital rectal examination (n=5) or both (n=4). Urine samples were taken before trans-rectal guided biopsy, immediately frozen and stored at −20° C. Subjects were assigned to two groups following pathological results of the prostate biopsy: Controls (n=18)-biopsy negative for CaP; and CaP (n=18)-biopsy positive for Cap.

Table 6 presents the clinical and pathological characteristics of the subjects. There were no significant differences between the various groups in age, mean PSA value, percent of positive Digital rectal exam, and percent of patients with previous negative prostate biopsies.

TABLE 6 patient and pathology characteristics

| | Controls (n = 18) | CaP (n = 18) | p |
|---|---|---|---|
| Age (years) | 67 ± 5.9 | 68 ± 6.8 | N.S. |
| Mean PSA (ng/ml) | 8.3 ± 6.1 | 8.9 ± 7.9 | N.S. |
| Percent of positive Digital Rectal Exam | 22% (4 pts) | 27% (5 pts) | N.S. |
| Percent of previous negative biopsy | 16% (3 pts) | 27% (5 pts) | N.S. |
| Number of patients with low risk CaP | Not relevant | 61% (11 pts) | |
| Number of patients with intermediate or high risk CaP | Not relevant | 39% (7 pts) | |

Reagents

Human HSP60 was prepared as described (6). HSP70 and HSP90 were purchased from StressGen Biotechnologies (Victoria, BC, Canada). Antibodies for detection of HSP60 and HSP90 were purchased from Santa Cruz Biotechnology (Santa Cruz, Calif.). Antibody for detection of HSP70 was purchased from SterssGen (Victoria, British Columbia, Canada). Elisa antibody sets for detection of IFNγ, TNFα, IL-1β and IL-2 were purchased from BioSource (Camarillo, Calif.). For IL-6, IL-10 and IL-8, sets were purchased from BioLegend (San Diego, Calif.). For IL-13 and TGFβ, sets were purchased from R&D Systems (Minneapolis, Minn.).

HSP Measurements

A direct enzyme-linked immunosorbent assay (ELISA) was used to quantify HSP concentrations in urine. Assays were done in triplicate according to the manufacturer's instructions. Minimal detection concentrations were 20 ng/ml for HSP60 and HSP70, and 5 ng/ml for HSP90.

Cytokine Urine Measurements

Sandwich ELISA was used to quantify cytokine concentrations in urine. The assays were done in triplicates according to the manufacturer's instructions. The minimal detection concentration was 30 pg/ml for each of the cytokines.

Statistical Analysis

Univariate analysis was performed to assess the differences between HSP and cytokine concentrations in the groups, using student t test. The National Cancer Institute recommends evaluating the performance of potential markers for cancer detection using receiver operating curves (ROC) (7). Therefore, we used ROC to calculate the area under the curve and the 95% confidence interval (AUC±95% CI) for association of the detected cytokines and PSA with biopsy positive CaP.

Example 6

HSP and Cytokine Urine Concentrations in CaP Patients

Figure 5A:
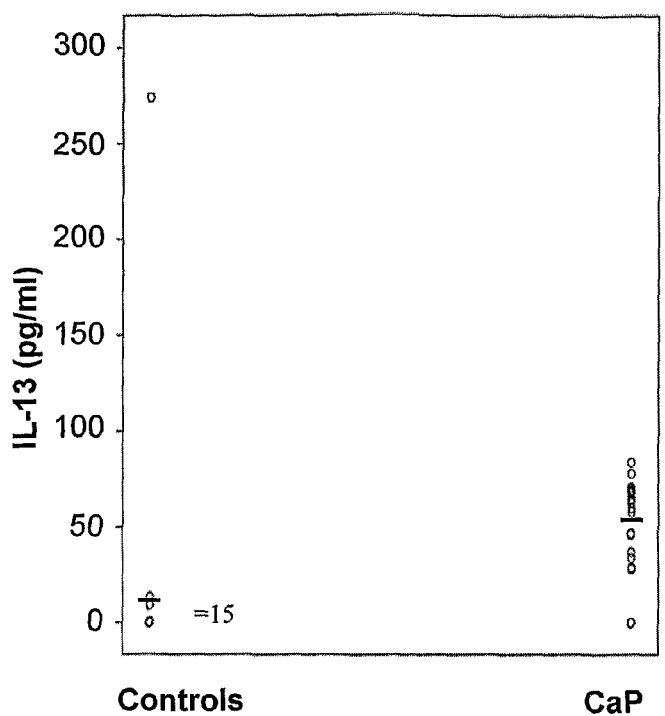
FIG. 5. Urinary concentrations of IL-13 and IL 1β. Urine was assayed by ELISA for the presence of IL-13(A) and IL-1β (B). The results are presented by a scatter plot—each dot represents one patient. One dot is presented when urinary concentrations overlap and the number of overlapping patients is indicated. *, $p< 0.05$ by student t-test.
Figure 5B:
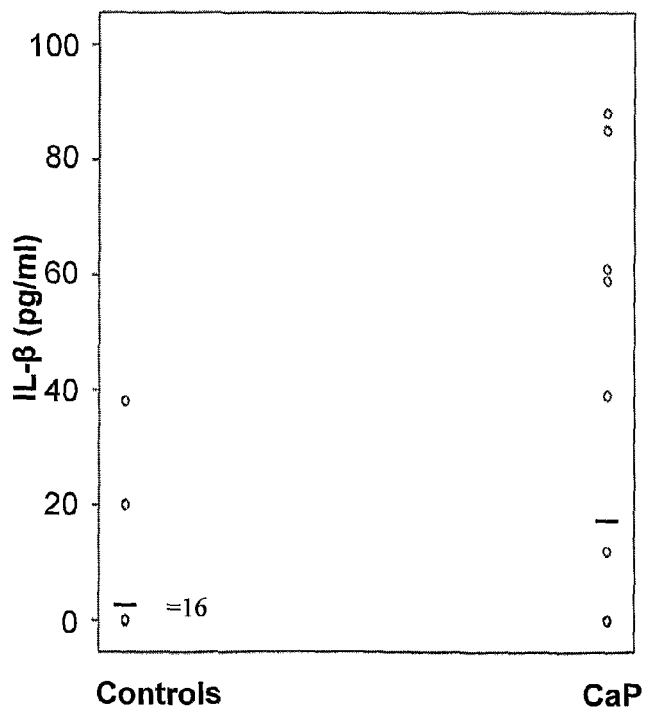

The concentrations of the various HSP's and cytokines in the urine were examined. HSP60, HSP70, HSP90, IFNγ, TNFα, IL-2, IL-6, IL-8, IL-10 and TGF-β were not detected; but IL-13 and IL-1β were detected. Urinary concentrations of IL-13 and IL-1β (FIG. 5 A,B) were significantly elevated in CaP patients compared to controls. Mean±SD values of IL-13 and IL-1β for CaP patients compared to controls were 50.4±24.8 vs. 16.4±33.5 pg/ml and 19.1±31 vs. 3.2±9.8 pg/ml (p<0.05 for all), respectively.

Example 7

IL-13 and IL-1β as Urinary Biomarkers for CaP

Figure 6:
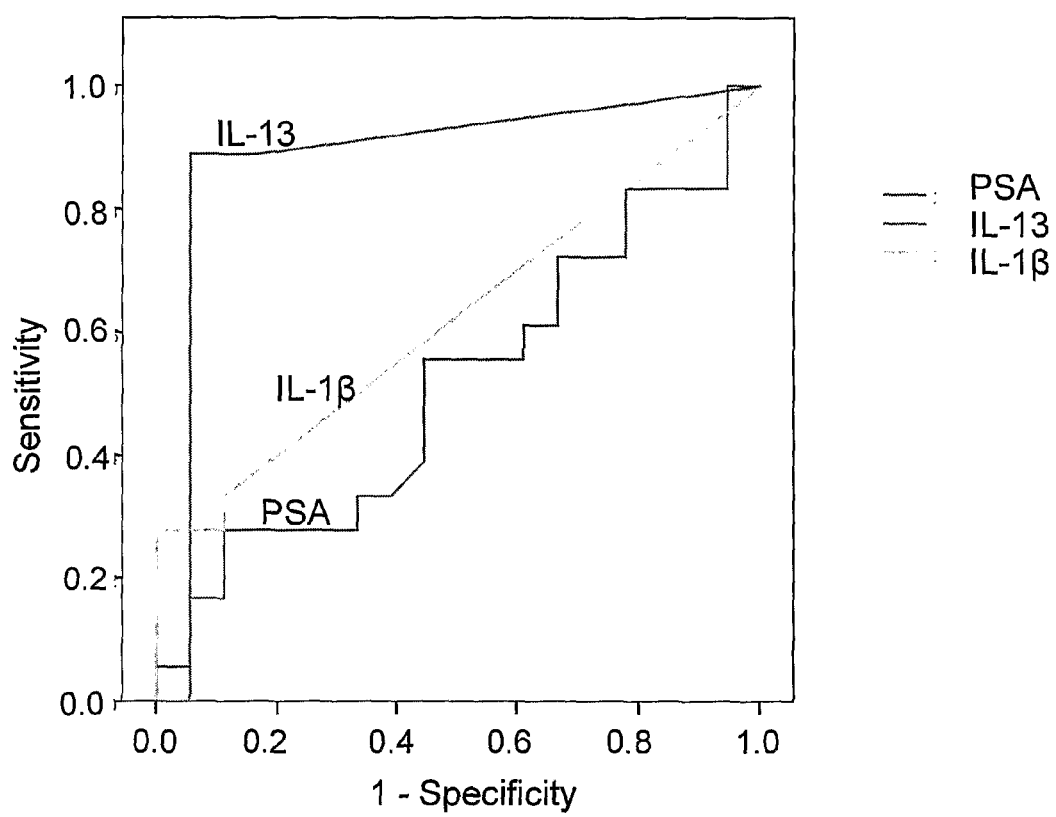
FIG. 6. ROC curve for IL-13, IL 1β and PSA for CaP detection.

A ROC analysis was used to determine the performance of IL-13 and IL-1β as markers for CaP according to the recommendation of the National Cancer Institute for early-phase biomarker development. FIG. 6 A demonstrate the ROC curve of IL-13 and IL-1β and PSA for CaP detection. IL-13 appeared to be the most prominent marker for CaP (AUC 0.88; 95% CI 0.75-0.95). However IL-1β is promising as well (AUC 0.62; 95% CI 0.45-0.80), both perform better than PSA.

REFERENCES

1. Bastacky S, Ibrahim S, Wilczynski S P, Murphy W M. The accuracy of urinary cytology in daily practice. *Cancer* 1999; 87(3):118-28.
2. van Rhijn B W, van der Poel H G, van der Kwast T H. Urine markers for bladder cancer surveillance: a systematic review. *Eur Urol* 2005; 47(6):736-48.
3. Lin W W, Karin M. A cytokine-mediated link between innate immunity, inflammation, and cancer. *J Clin Invest* 2007; 117(5):1175-83.
4. Quintana F J, Rotem A, Carmi P, Cohen I R. Vaccination with empty plasmid DNA or CpG oligonucleotide inhibits diabetes in nonobese diabetic mice: modulation of spontaneous 60-kDa heat shock protein autoimmunity. *J Immunol* 2000; 165(10:6148-55.
5. Pepe M S, Etzioni R, Feng Z, et al. Phases of biomarker development for early detection of cancer. *J Natl Cancer Inst* 2001; 93(14):1054-61.
6. Lindquist S, Craig E A. The heat-shock proteins. *Annu Rev Genet* 1988;22:631-77.
7. Kaufmann S H. Heat shock proteins and the immune response. *Immunol Today* 1990; 11(4): 129-36.
8. Levine A J, Momand J, Finlay C A. The p53 tumour suppressor gene. *Nature* 1991; 351(6326):453-6.
9. Ciocca D R, Clark G M, Tandon A K, Fuqua S A, Welch W J, McGuire W L. Heat shock protein hsp70 in patients with axillary lymph node-negative breast cancer: prognostic implications. *J Natl Cancer Inst* 1993; 85(7):570-4.
10. Cappello F, de Macario E C, Marasa L, Zummo G, Macario A J. Hsp60 expression, new locations, functions and perspectives for cancer diagnosis and therapy. *Cancer Biol Ther* 2008; 7(6):801-9.
11. Fuller K J, Issels R D, Slosman D O, Guillet J G, Soussi T, Polla B S. Cancer and the heat shock response. *Eur J Cancer* 1994; 30A(12):1884-91.
12. Lebret T, Watson R W, Molinie V, et al. Heat shock proteins HSP27, HSP60, HSP70, and HSP90: expression in bladder carcinoma. *Cancer* 2003; 98(5):970-7.
13. Lebret T, Watson R W, Molinie V, et al. HSP90 expression: a new predictive factor for BCG response in stage Ta-T1 grade 3 bladder tumours. *Eur Urol* 2007; 51(1):161-6; discussion 166-7.
14. Bohle A, Nowc C, Ulmer A J, et al. Elevations of cytokines interleukin-1, interleukin-2 and tumor necrosis factor in the urine of patients after intravesical bacillus Calmette-Guerin immunotherapy. *J Urol* 1990; 144(1):59-64.
15. Fleischmann J D, Toossi Z, Ellner J J, Wentworth D B, Ratliff T L, Imbembo A L. Urinary interleukins in patients receiving intravesical Bacillus Calmette-Guerin therapy for superficial bladder cancer. *Cancer* 1989; 64(7):1447-54.
16. Saint F, Patard J J, Maille P, et al. T helper ½ lymphocyte urinary cytokine profiles in responding and nonresponding patients after 1 and 2 courses of bacillus Calmette-Guerin for superficial bladder cancer. *J Urol* 2001; 166(6):2142-7.
17. Loskog A, Ninalga C, Paul-Wetterberg G, de la Tone M, Malmstrom P U, Totterman T H. Human bladder carcinoma is dominated by T-regulatory cells and Th1 inhibitory cytokines. *J Urol* 2007; 177(1):353-8.
18. Helmy A, Hammam O A, El Lithy T R, El Deen Wishahi M M. The role of TGF-beta-1 protein and TGF-beta-R-1 receptor in immune escape mechanism in bladder cancer. *MedGenMed* 2007; 9(4):34.
19. Minty A, Chalon P, Derocq J M, et al. Interleukin-13 is a new human lymphokine regulating inflammatory and immune responses. *Nature* 1993; 362(6417):248-50.
20. McKenzie A N, Culpepper J A, de Waal Malefyt R, et al. Interleukin 13, a T-cell-derived cytokine that regulates human monocyte and B-cell function. *Proc Natl Acad Sci USA* 1993; 90(8):3735-9.
21. Punnonen J, Aversa G, Cocks B G, et al. Interleukin 13 induces interleukin 4-independent IgG4 and IgE synthesis and CD23 expression by human B cells. *Proc Natl Acad Sci USA* 1993; 90(8):3730-4.
22. Schmid-Grendelmeier P, Altznauer F, Fischer B, et al. Eosinophils express functional IL-13 in eosinophilic inflammatory diseases. *J Immunol* 2002; 169(2): 1021-7.
23. Brown K D, Zurawski S M, Mosmann T R, Zurawski G. A family of small inducible proteins secreted by leukocytes are members of a new superfamily that includes leukocyte and fibroblast-derived inflammatory agents, growth factors, and indicators of various activation processes. *J Immunol* 1989; 142(2):679-87.
24. Terabe M, Matsui S, Noben-Trauth N, et al. NKT cell-mediated repression of tumor immunosurveillance by IL-13 and the IL-4R-STAT6 pathway. *Nat Immunol* 2000; 1(6):515-20.
25. Skinnider B F, Elia A J, Gascoyne R D, et al. Interleukin 13 and interleukin 13 receptor are frequently expressed by Hodgkin and Reed-Sternberg cells of Hodgkin lymphoma. *Blood* 2001; 97(1):250-5.
26. Kapp U, Yeh W C, Patterson B, et al. Interleukin 13 is secreted by and stimulates the growth of Hodgkin and Reed-Sternberg cells. *J Exp Med* 1999; 189(12):1939-46.
27. Raz I, Elias D, Avron A, Tamir M, Metzger M, Cohen I R. Beta-cell function in new-onset type 1 diabetes and immunomodulation with a heat-shock protein peptide (DiaPep277): a randomised, double-blind, phase II trial. *Lancet* 2001; 358(9295):1749-53.
28. Cai T, Mazzoli S, Meacci F, Tinacci G, Nesi G, Zini E, Bartoletti R. Interleukin-6/10 ratio as a prognostic marker of recurrence in patients with intermediate risk urothelial bladder carcinoma. J Urol. 2007 November; 178(5):1906-11; discussion 1911-2. Epub 2007 Sep. 17.
29. Koçak H, Oner-Iyidoğan Y, Kook T, Oner P. Determination of diagnostic and prognostic values of urinary interleukin-8, tumor necrosis factor-alpha, and leukocyte arylsulfatase-A activity in patients with bladder cancer. Clin Biochem. 2004 August; 37(8):673-8.
30. Sheryka E, Wheeler M A, Hausladen D A, Weiss R M. Urinary interleukin-8 levels are elevated in subjects with transitional cell carcinoma. Urology. 2003 July; 62(1):162-6.
31. Esuvaranathan K, Alexandroff A B, McIntyre M, Jackson A M, Prescott S, Chisholm G D, James K. Interleukin-6 production by bladder tumors is upregulated by BCG immunotherapy. J Urol. 1995 Auguat; 154(2 Pt 1):572-5.
32. McDavid, J. Lee, J. P. Fulton, J. Tonita and T. D. Thompson, Prostate cancer incidence and mortality rates and trends in the United States and Canada, Public Health Rep. 2004; 119 (2):174-186.
33. Andriole G L, Crawford E D, Grubb R L 3rd, Buys S S, Chia D, Church T R et al. Mortality results from a randomized prostate-cancer screening trial. N Engl J Med. 2009; 360(13):1310-9.

34. Schröder F H, Hugosson J, Roobol M J, Tammela T L, Ciatto S, Nelen V et al. Screening and prostate-cancer mortality in a randomized European study. N Engl J Med. 2009; 360(13):1320-8.
35. J. E. Damber and G. Aus, Prostate cancer, Lancet 2008; 371 (9625):1710-1721.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for assessing the presence of bladder cancer in a subject suspected of having bladder cancer, said method comprising:
   (a) obtaining from the subject a urine sample substantially free of residual cells;
   (b) determining the level of at least one biomarker in the urine sample, said at least one biomarker being selected from the group consisting of IL-13; HSP60; HSP70; HSP90; and IL-10;
   (c) comparing the level of said at least one biomarker to a control value or level corresponding to a set of one or more healthy individuals; and
   (d) determining the presence of bladder cancer in the subject if there is a significant elevation in the level of the at least one biomarker in said urine sample compared to the control value.

2. The method of claim 1, wherein the at least one biomarker is selected from the group consisting of IL-13, IL-10 and HSP60.

3. The method of claim 2, wherein the at least one biomarker is IL-13.

4. The method of claim 1, wherein the step of determining the level of the at least one biomarker comprises determining the levels of a plurality of biomarkers selected from the group consisting of IL-13, IL-10, IL-8, HSP60, HSP70 and HSP90, and wherein significant elevation in the levels of the plurality of said biomarkers compared to the control values indicates that said subject is afflicted with bladder cancer.

5. The method of claim 4, wherein the plurality of biomarkers includes at least one heat shock protein from the group consisting of HSP60, HSP70 and HSP90; and at least one cytokine from the group consisting of IL-13, IL-10, and IL-8.

6. The method of claim 1, wherein the control value is selected from the group consisting of a value obtained from a healthy control individual, a panel of control values from a set of healthy individuals, and a stored set of data corresponding to control individuals that are not afflicted with bladder cancer.

7. The method of claim 1, wherein the cancer is transitional cell carcinoma.

8. The method of claim 1, wherein the subject is either symptomatic or asymptomatic.

9. The method of claim 1, further comprising filtering the urine sample through a filter with a cutoff of no more than 30 kD, reconstituting the urine sample, and then diluting the urine sample at least 1:2 before performing step (b).

10. The method of claim 1, wherein said step of determining the level of biomarker in the urine sample is performed by an immunoassay.

11. A method for assessing the presence of muscle invasive bladder cancer in a subject suspected of having muscle invasive bladder cancer, said method comprising:
    (a) obtaining from the subject a urine sample substantially free of residual cells;
    (b) determining the level of at least one biomarker in the urine sample, said at least one biomarker being selected from the group consisting of HSP60, HSP70 and HSP90;
    (c) comparing the level of said at least one biomarker to a control value corresponding to one or more healthy individuals; and
    (d) determining the presence of bladder cancer in the subject if there is a significant elevation in the level of the at least one biomarker compared to the control value.

12. The method of claim 11, wherein the at least one biomarker is HSP60.

13. The method of claim 11, wherein said step of determining the level of at least one biomarker comprises determining the levels of a plurality of biomarkers selected from the group consisting of IL-13, HSP60, HSP70, HSP90, IL-8, IL-6 and TGF-13, and wherein a significant elevation in the levels of the plurality of biomarkers compared to the control value indicates that said subject is afflicted with muscle invasive bladder cancer.

14. The method of claim 13, wherein the plurality of biomarkers comprise HSP60, HSP70 and HSP90.

15. The method according to claim 11, wherein the control value is selected from the group consisting of a value obtained from an individual having non-invasive bladder cancer, a panel of control values obtained from individuals having non-invasive bladder cancer, and a stored set of data corresponding to control individuals that are afflicted with non-invasive bladder cancer.

16. The method of claim 11, further comprising filtering the urine sample through a filter with a cutoff of no more than 30 kD, reconstituting the urine sample, and then diluting the urine sample at least 1:2 before performing step (b).

17. The method of claim 11, wherein said step of determining the level of biomarker in the urine sample is performed by an immunoassay.

18. A method for diagnosing bladder cancer in a subject suspected of having bladder cancer, said method comprising:
    (a) obtaining from the subject a urine sample substantially free of residual cells;
    (b) determining the level of the biomarkers IL-13, HSP60, HSP70 and HSP90 in the urine sample;
    (c) comparing the level of at least one biomarker listed in step (b) to a negative control value corresponding to the level in a healthy individual or to a positive control value corresponding to the level in an individual having non-invasive bladder cancer; and
    (d) assessing the presence or absence of bladder cancer in the subject based on the comparison in step (c),
    wherein:
        (i) a significant elevation in the level of IL-13 compared to the negative control value indicates that said subject is afflicted with bladder cancer;
        (ii) a significant elevation in the level of HSP60, HSP70 and HSP90 compared to the positive control value indicates that said subject is afflicted with invasive bladder cancer; and
        (iii) a level of HSP60, HSP70 and HSP90 which is not significantly elevated compared to the positive control value indicates that the subject has non-invasive bladder cancer.

19. The method of claim 18, further comprising filtering the urine sample through a filter with a cutoff of no more than 30 kD, reconstituting the urine sample, and then diluting the urine sample at least 1:2 before performing step (b).

20. The method of claim 18, wherein said step of determining the level of biomarker in the urine sample is performed by an immunoassay.

21. A method for assessing the presence of genitourinary cancer in a subject suspected of having genitourinary cancer, said method comprising:
    (a) obtaining from the subject a urine sample substantially free of residual cells;
    (b) determining the level of IL-13 in the urine sample;
    (c) comparing the level of said IL-13 in said urine sample to a control value corresponding to a healthy individual; and (d) determining the presence of genitourinary cancer in the subject if there is a significant elevation in the level of IL-13 compared to the control value.

22. The method of claim 21, wherein the genitourinary cancer is selected from group consisting of bladder cancer and prostate cancer.

23. The method of claim 21, further comprising determining the level of at least one biomarker selected from the group consisting of:
  determining the levels of at least one heat shock protein selected from the group consisting of HSP60, HSP70 and HSP90 wherein a significant elevation in the level of at least one HSP compared to a control value corresponding to a healthy individual indicates that said subject is afflicted with bladder cancer;
  determining the levels of at least one additional cytokine selected from the group consisting of IL-10 and IL-8 wherein a significant elevation in the level of at least one cytokine compared to a control value corresponding to a healthy individual indicates that said subject is afflicted with bladder cancer;
  determining the levels of IL-1β wherein a significant elevation in the level of IL-1β compared to a control value corresponding to a healthy individual indicates that said subject is afflicted with prostate cancer; or
  determining the level of at least one biomarker selected from the group consisting of HSP60, HSP70, HSP90, IL-10, IL-8 and IL-1β, wherein:
  (i) a significant elevation in the level of IL-13 and at least one biomarker selected from the group consisting of HSP60, HSP70, HSP90, IL-10 and IL-8 compared to a control value corresponding to a healthy individual indicates that said subject is afflicted with bladder cancer; and
  (ii) a significant elevation in the level of IL-13 and the IL-1β biomarker compared to a control value corresponding to a healthy individual indicates that said subject is afflicted with prostate cancer.

24. The method of claim 21, further comprising filtering the urine sample through a filter with a cutoff of no more than 30 kD, reconstituting the urine sample and then diluting the urine sample at least 1:2 before performing step (b).

25. The method of claim 23, wherein said genitourinary cancer is prostate cancer and said step of determining the presence of genitourinary cancer in the patient comprises determining the presence of prostate cancer in the patient if there is a significant elevation in the level IL-13 and IL-1β compared to a control value corresponding to a healthy individual.

26. The method of claim 21, wherein said step of determining the level of IL-13 in the urine sample is performed by an immunoassay.

* * * * *

SEQUENCE LISTING

```
<160> NUMBER OF SEQ ID NOS: 9

<210> SEQ ID NO 1
<211> LENGTH: 146
<212> TYPE: PRT
<213> ORGANISM: Homo sapiens

<400> SEQUENCE: 1

Met His Pro Leu Leu Asn Pro Leu Leu Leu Ala Leu Gly Leu Met Ala
1               5                   10                  15

Leu Leu Leu Thr Thr Val Ile Ala Leu Thr Cys Leu Gly Gly Phe Ala
            20                  25                  30

Ser Pro Gly Pro Val Pro Pro Ser Thr Ala Leu Arg Glu Leu Ile Glu
        35                  40                  45

Glu Leu Val Asn Ile Thr Gln Asn Gln Lys Ala Pro Leu Cys Asn Gly
    50                  55                  60

Ser Met Val Trp Ser Ile Asn Leu Thr Ala Gly Met Tyr Cys Ala Ala
65                  70                  75                  80

Leu Glu Ser Leu Ile Asn Val Ser Gly Cys Ser Ala Ile Glu Lys Thr
                85                  90                  95

Gln Arg Met Leu Ser Gly Phe Cys Pro His Lys Val Ser Ala Gly Gln
            100                 105                 110

Phe Ser Ser Leu His Val Arg Asp Thr Lys Ile Glu Val Ala Gln Phe
        115                 120                 125

Val Lys Asp Leu Leu Leu His Leu Lys Lys Leu Phe Arg Glu Gly Arg
    130                 135                 140

Phe Asn
145

<210> SEQ ID NO 2
<211> LENGTH: 212
<212> TYPE: PRT
<213> ORGANISM: Homo sapiens

<400> SEQUENCE: 2

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95
```

-continued

```
Glu Lys Asp Gly Cys Phe Gln Ser Gly Phe Asn Glu Glu Thr Cys Leu
            100                 105                 110
Val Lys Ile Ile Thr Gly Leu Leu Glu Phe Glu Val Tyr Leu Glu Tyr
        115                 120                 125
Leu Gln Asn Arg Phe Glu Ser Glu Glu Gln Arg Ala Val Gln
    130                 135                 140
Met Ser Thr Lys Val Leu Ile Gln Phe Leu Gln Lys Lys Ala Lys Asn
145                 150                 155                 160
Leu Asp Ala Ile Thr Thr Pro Asp Pro Thr Thr Asn Ala Ser Leu Leu
                165                 170                 175
Thr Lys Leu Gln Ala Gln Asn Gln Trp Leu Gln Asp Met Thr Thr His
            180                 185                 190
Leu Ile Leu Arg Ser Phe Lys Glu Phe Leu Gln Ser Ser Leu Arg Ala
            195                 200                 205
Leu Arg Gln Met
    210

<210> SEQ ID NO 3
<211> LENGTH: 99
<212> TYPE: PRT
<213> ORGANISM: Homo sapiens

<400> SEQUENCE: 3

Met Thr Ser Lys Leu Ala Val Ala Leu Leu Ala Ala Phe Leu Ile Ser
1               5                   10                  15
Ala Ala Leu Cys Glu Gly Ala Val Leu Pro Arg Ser Ala Lys Glu Leu
            20                  25                  30
Arg Cys Gln Cys Ile Lys Thr Tyr Ser Lys Pro Phe His Pro Lys Phe
        35                  40                  45
Ile Lys Glu Leu Arg Val Ile Glu Ser Gly Pro His Cys Ala Asn Thr
    50                  55                  60
Glu Ile Ile Val Lys Leu Ser Asp Gly Arg Glu Leu Cys Leu Asp Pro
65                  70                  75                  80
Lys Glu Asn Trp Val Gln Arg Val Val Glu Lys Phe Leu Lys Arg Ala
                85                  90                  95
Glu Asn Ser

<210> SEQ ID NO 4
<211> LENGTH: 178
<212> TYPE: PRT
<213> ORGANISM: Homo sapiens

<400> SEQUENCE: 4

Met His Ser Ser Ala Leu Leu Cys Cys Leu Val Leu Leu Thr Gly Val
1               5                   10                  15
Arg Ala Ser Pro Gly Gln Gly Thr Gln Ser Glu Asn Ser Cys Thr His
            20                  25                  30
Phe Pro Gly Asn Leu Pro Asn Met Leu Arg Asp Leu Arg Asp Ala Phe
        35                  40                  45
Ser Arg Val Lys Thr Phe Phe Gln Met Lys Asp Gln Leu Asp Asn Leu
    50                  55                  60
Leu Leu Lys Glu Ser Leu Leu Glu Asp Phe Lys Gly Tyr Leu Gly Cys
65                  70                  75                  80
Gln Ala Leu Ser Glu Met Ile Gln Phe Tyr Leu Glu Glu Val Met Pro
                85                  90                  95
Gln Ala Glu Asn Gln Asp Pro Asp Ile Lys Ala His Val Asn Ser Leu
```

```
                   100                 105                 110
Gly Glu Asn Leu Lys Thr Leu Arg Leu Arg Leu Arg Cys His Arg
            115                 120                 125

Phe Leu Pro Cys Glu Asn Lys Ser Lys Ala Val Glu Gln Val Lys Asn
        130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn

<210> SEQ ID NO 5
<211> LENGTH: 390
<212> TYPE: PRT
<213> ORGANISM: Homo sapiens

<400> SEQUENCE: 5

Met Pro Pro Ser Gly Leu Arg Leu Leu Leu Leu Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
    290                 295                 300
```

```
Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
            325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
            355                 360                 365

Tyr Val Gly Arg Lys Pro Lys Val Glu Gln Leu Ser Asn Met Ile Val
            370                 375                 380

Arg Ser Cys Lys Cys Ser
385                 390

<210> SEQ ID NO 6
<211> LENGTH: 573
<212> TYPE: PRT
<213> ORGANISM: Homo sapiens

<400> SEQUENCE: 6

Met Leu Arg Leu Pro Thr Val Phe Arg Gln Met Arg Pro Val Ser Arg
1               5                   10                  15

Val Leu Ala Pro His Leu Thr Arg Ala Tyr Ala Lys Asp Val Lys Phe
            20                  25                  30

Gly Ala Asp Ala Arg Ala Leu Met Leu Gln Gly Val Asp Leu Leu Ala
        35                  40                  45

Asp Ala Val Ala Val Thr Met Gly Pro Lys Gly Arg Thr Val Ile Ile
    50                  55                  60

Glu Gln Ser Trp Gly Ser Pro Lys Val Thr Lys Asp Gly Val Thr Val
65                  70                  75                  80

Ala Lys Ser Ile Asp Leu Lys Asp Lys Tyr Lys Asn Ile Gly Ala Lys
                85                  90                  95

Leu Val Gln Asp Val Ala Asn Asn Thr Asn Glu Glu Ala Gly Asp Gly
            100                 105                 110

Thr Thr Thr Ala Thr Val Leu Ala Arg Ser Ile Ala Lys Glu Gly Phe
        115                 120                 125

Glu Lys Ile Ser Lys Gly Ala Asn Pro Val Glu Ile Arg Arg Gly Val
    130                 135                 140

Met Leu Ala Val Asp Ala Val Ile Ala Glu Leu Lys Lys Gln Ser Lys
145                 150                 155                 160

Pro Val Thr Thr Pro Glu Glu Ile Ala Gln Val Ala Thr Ile Ser Ala
                165                 170                 175

Asn Gly Asp Lys Glu Ile Gly Asn Ile Ile Ser Asp Ala Met Lys Lys
            180                 185                 190

Val Gly Arg Lys Gly Val Ile Thr Val Lys Asp Gly Lys Thr Leu Asn
        195                 200                 205

Asp Glu Leu Glu Ile Ile Glu Gly Met Lys Phe Asp Arg Gly Tyr Ile
    210                 215                 220

Ser Pro Tyr Phe Ile Asn Thr Ser Lys Gly Gln Lys Cys Glu Phe Gln
225                 230                 235                 240

Asp Ala Tyr Val Leu Leu Ser Glu Lys Lys Ile Ser Ser Ile Gln Ser
                245                 250                 255

Ile Val Pro Ala Leu Glu Ile Ala Asn Ala His Arg Lys Pro Leu Val
            260                 265                 270

Ile Ile Ala Glu Asp Val Asp Gly Glu Ala Leu Ser Thr Leu Val Leu
        275                 280                 285
```

Asn Arg Leu Lys Val Gly Leu Gln Val Val Ala Val Lys Ala Pro Gly
            290                 295                 300

Phe Gly Asp Asn Arg Lys Asn Gln Leu Lys Asp Met Ala Ile Ala Thr
305                 310                 315                 320

Gly Gly Ala Val Phe Gly Glu Gly Leu Thr Leu Asn Leu Glu Asp
            325                 330                 335

Val Gln Pro His Asp Leu Gly Lys Val Gly Glu Val Ile Val Thr Lys
            340                 345                 350

Asp Asp Ala Met Leu Leu Lys Gly Lys Gly Asp Lys Ala Gln Ile Glu
            355                 360                 365

Lys Arg Ile Gln Glu Ile Ile Glu Gln Leu Asp Val Thr Thr Ser Glu
            370                 375                 380

Tyr Glu Lys Glu Lys Leu Asn Glu Arg Leu Ala Lys Leu Ser Asp Gly
385                 390                 395                 400

Val Ala Val Leu Lys Val Gly Gly Thr Ser Asp Val Glu Val Asn Glu
            405                 410                 415

Lys Lys Asp Arg Val Thr Asp Ala Leu Asn Ala Thr Arg Ala Ala Val
            420                 425                 430

Glu Glu Gly Ile Val Leu Gly Gly Gly Cys Ala Leu Leu Arg Cys Ile
            435                 440                 445

Pro Ala Leu Asp Ser Leu Thr Pro Ala Asn Glu Asp Gln Lys Ile Gly
450                 455                 460

Ile Glu Ile Ile Lys Arg Thr Leu Lys Ile Pro Ala Met Thr Ile Ala
465                 470                 475                 480

Lys Asn Ala Gly Val Glu Gly Ser Leu Ile Val Glu Lys Ile Met Gln
            485                 490                 495

Ser Ser Ser Glu Val Gly Tyr Asp Ala Met Ala Gly Asp Phe Val Asn
            500                 505                 510

Met Val Glu Lys Gly Ile Ile Asp Pro Thr Lys Val Val Arg Thr Ala
            515                 520                 525

Leu Leu Asp Ala Ala Gly Val Ala Ser Leu Leu Thr Thr Ala Glu Val
            530                 535                 540

Val Val Thr Glu Ile Pro Lys Glu Glu Lys Asp Pro Gly Met Gly Ala
545                 550                 555                 560

Met Gly Gly Met Gly Gly Gly Met Gly Gly Gly Met Phe
            565                 570

<210> SEQ ID NO 7
<211> LENGTH: 641
<212> TYPE: PRT
<213> ORGANISM: Homo sapiens

<400> SEQUENCE: 7

Met Ala Lys Ala Ala Ile Gly Ile Asp Leu Gly Thr Thr Tyr Ser
1               5                   10                  15

Cys Val Gly Val Phe Gln His Gly Lys Val Glu Ile Ile Ala Asn Asp
            20                  25                  30

Gln Gly Asn Arg Thr Thr Pro Ser Tyr Val Ala Phe Thr Asp Thr Glu
            35                  40                  45

Arg Leu Ile Gly Asp Ala Ala Lys Asn Gln Val Ala Leu Asn Pro Gln
50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Gln Val Ile Asn
            85                  90                  95

```
Asp Gly Asp Lys Pro Lys Val Gln Val Ser Tyr Lys Gly Glu Thr Lys
            100                 105                 110

Ala Phe Tyr Pro Glu Glu Ile Ser Ser Met Val Leu Thr Lys Met Lys
        115                 120                 125

Glu Ile Ala Glu Ala Tyr Leu Gly Tyr Pro Val Thr Asn Ala Val Ile
    130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
    210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
    290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
            340                 345                 350

Phe Phe Asn Gly Arg Asp Leu Asn Lys Ser Ile Asn Pro Asp Glu Ala
        355                 360                 365

Val Ala Tyr Gly Ala Ala Val Gln Ala Ala Ile Leu Met Gly Asp Lys
    370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg
                405                 410                 415

Asn Ser Thr Ile Pro Thr Lys Gln Thr Gln Ile Phe Thr Thr Tyr Ser
            420                 425                 430

Asp Asn Gln Pro Gly Val Leu Ile Gln Val Tyr Glu Gly Glu Arg Ala
        435                 440                 445

Met Thr Lys Asp Asn Asn Leu Leu Gly Arg Phe Glu Leu Ser Gly Ile
    450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
            500                 505                 510

Glu Glu Ile Glu Arg Met Val Gln Glu Ala Glu Lys Tyr Lys Ala Glu
```

```
                515                 520                 525
Asp Glu Val Gln Arg Glu Arg Val Ser Ala Lys Asn Ala Leu Glu Ser
            530                 535                 540

Tyr Ala Phe Asn Met Lys Ser Ala Val Glu Asp Glu Gly Leu Lys Gly
545                 550                 555                 560

Lys Ile Ser Glu Ala Asp Lys Lys Val Leu Asp Lys Cys Gln Glu
                565                 570                 575

Val Ile Ser Trp Leu Asp Ala Asn Thr Leu Ala Glu Lys Asp Glu Phe
            580                 585                 590

Glu His Lys Arg Lys Glu Leu Glu Gln Val Cys Asn Pro Ile Ile Ser
                595                 600                 605

Gly Leu Tyr Gln Gly Ala Gly Gly Pro Gly Pro Gly Gly Phe Gly Ala
            610                 615                 620

Gln Gly Pro Lys Gly Gly Ser Gly Ser Gly Pro Thr Ile Glu Glu Val
625                 630                 635                 640

Asp

<210> SEQ ID NO 8
<211> LENGTH: 732
<212> TYPE: PRT
<213> ORGANISM: Homo sapiens

<400> SEQUENCE: 8

Met Pro Glu Glu Thr Gln Thr Gln Asp Gln Pro Met Glu Glu Glu Glu
1               5                   10                  15

Val Glu Thr Phe Ala Phe Gln Ala Glu Ile Ala Gln Leu Met Ser Leu
                20                  25                  30

Ile Ile Asn Thr Phe Tyr Ser Asn Lys Glu Ile Phe Leu Arg Glu Leu
            35                  40                  45

Ile Ser Asn Ser Ser Asp Ala Leu Asp Lys Ile Arg Tyr Glu Ser Leu
        50                  55                  60

Thr Asp Pro Ser Lys Leu Asp Ser Gly Lys Glu Leu His Ile Asn Leu
65                  70                  75                  80

Ile Pro Asn Lys Gln Asp Arg Thr Leu Thr Ile Val Asp Thr Gly Ile
                85                  90                  95

Gly Met Thr Lys Ala Asp Leu Ile Asn Asn Leu Gly Thr Ile Ala Lys
            100                 105                 110

Ser Gly Thr Lys Ala Phe Met Glu Ala Leu Gln Ala Gly Ala Asp Ile
        115                 120                 125

Ser Met Ile Gly Gln Phe Gly Val Gly Phe Tyr Ser Ala Tyr Leu Val
130                 135                 140

Ala Glu Lys Val Thr Val Ile Thr Lys His Asn Asp Asp Glu Gln Tyr
145                 150                 155                 160

Ala Trp Glu Ser Ser Ala Gly Gly Ser Phe Thr Val Arg Thr Asp Thr
                165                 170                 175

Gly Glu Pro Met Gly Arg Gly Thr Lys Val Ile Leu His Leu Lys Glu
            180                 185                 190

Asp Gln Thr Glu Tyr Leu Glu Glu Arg Arg Ile Lys Glu Ile Val Lys
        195                 200                 205

Lys His Ser Gln Phe Ile Gly Tyr Pro Ile Thr Leu Phe Val Glu Lys
210                 215                 220

Glu Arg Asp Lys Glu Val Ser Asp Asp Glu Ala Glu Glu Lys Glu Asp
225                 230                 235                 240

Lys Glu Glu Glu Lys Glu Lys Glu Glu Lys Glu Ser Glu Asp Lys Pro
                245                 250                 255
```

-continued

```
Glu Ile Glu Asp Val Gly Ser Asp Glu Glu Glu Lys Lys Asp Gly
            260                 265                 270

Asp Lys Lys Lys Lys Lys Ile Lys Glu Lys Tyr Ile Asp Gln Glu
            275                 280                 285

Glu Leu Asn Lys Thr Lys Pro Ile Trp Thr Arg Asn Pro Asp Asp Ile
            290                 295                 300

Thr Asn Glu Glu Tyr Gly Glu Phe Tyr Lys Ser Leu Thr Asn Asp Trp
305                 310                 315                 320

Glu Asp His Leu Ala Val Lys His Phe Ser Val Glu Gly Gln Leu Glu
                325                 330                 335

Phe Arg Ala Leu Leu Phe Val Pro Arg Arg Ala Pro Phe Asp Leu Phe
                340                 345                 350

Glu Asn Arg Lys Lys Lys Asn Asn Ile Lys Leu Tyr Val Arg Arg Val
                355                 360                 365

Phe Ile Met Asp Asn Cys Glu Glu Leu Ile Pro Glu Tyr Leu Asn Phe
                370                 375                 380

Ile Arg Gly Val Val Asp Ser Glu Asp Leu Pro Leu Asn Ile Ser Arg
385                 390                 395                 400

Glu Met Leu Gln Gln Ser Lys Ile Leu Lys Val Ile Arg Lys Asn Leu
                405                 410                 415

Val Lys Lys Cys Leu Glu Leu Phe Thr Glu Leu Ala Glu Asp Lys Glu
                420                 425                 430

Asn Tyr Lys Lys Phe Tyr Glu Gln Phe Ser Lys Asn Ile Lys Leu Gly
                435                 440                 445

Ile His Glu Asp Ser Gln Asn Arg Lys Lys Leu Ser Glu Leu Leu Arg
                450                 455                 460

Tyr Tyr Thr Ser Ala Ser Gly Asp Glu Met Val Ser Leu Lys Asp Tyr
465                 470                 475                 480

Cys Thr Arg Met Lys Glu Asn Gln Lys His Ile Tyr Tyr Ile Thr Gly
                485                 490                 495

Glu Thr Lys Asp Gln Val Ala Asn Ser Ala Phe Val Glu Arg Leu Arg
                500                 505                 510

Lys His Gly Leu Glu Val Ile Tyr Met Ile Glu Pro Ile Asp Glu Tyr
                515                 520                 525

Cys Val Gln Gln Leu Lys Glu Phe Glu Gly Lys Thr Leu Val Ser Val
                530                 535                 540

Thr Lys Glu Gly Leu Glu Leu Pro Glu Asp Glu Glu Lys Lys Lys
545                 550                 555                 560

Gln Glu Glu Lys Lys Thr Lys Phe Glu Asn Leu Cys Lys Ile Met Lys
                565                 570                 575

Asp Ile Leu Glu Lys Lys Val Glu Lys Val Val Val Ser Asn Arg Leu
                580                 585                 590

Val Thr Ser Pro Cys Cys Ile Val Thr Ser Thr Tyr Gly Trp Thr Ala
                595                 600                 605

Asn Met Glu Arg Ile Met Lys Ala Gln Ala Leu Arg Asp Asn Ser Thr
                610                 615                 620

Met Gly Tyr Met Ala Ala Lys Lys His Leu Glu Ile Asn Pro Asp His
625                 630                 635                 640

Ser Ile Ile Glu Thr Leu Arg Gln Lys Ala Glu Ala Asp Lys Asn Asp
                645                 650                 655

Lys Ser Val Lys Asp Leu Val Ile Leu Leu Tyr Glu Thr Ala Leu Leu
                660                 665                 670

Ser Ser Gly Phe Ser Leu Glu Asp Pro Gln Thr His Ala Asn Arg Ile
```

```
            675                 680                 685
Tyr Arg Met Ile Lys Leu Gly Leu Gly Ile Asp Glu Asp Pro Thr
690                 695                 700

Ala Asp Asp Thr Ser Ala Ala Val Thr Glu Glu Met Pro Pro Leu Glu
705                 710                 715                 720

Gly Asp Asp Asp Thr Ser Arg Met Glu Glu Val Asp
                725                 730

<210> SEQ ID NO 9
<211> LENGTH: 269
<212> TYPE: PRT
<213> ORGANISM: Homo sapiens

<400> SEQUENCE: 9

Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
                20                  25                  30

Lys Cys Ser Phe Gln Asp Leu Asp Leu Cys Pro Leu Asp Gly Gly Ile
            35                  40                  45

Gln Leu Arg Ile Ser Asp His His Tyr Ser Lys Gly Phe Arg Gln Ala
    50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
            100                 105                 110

Tyr Val His Asp Ala Pro Val Arg Ser Leu Asn Cys Thr Leu Arg Asp
    115                 120                 125

Ser Gln Gln Lys Ser Leu Val Met Ser Gly Pro Tyr Glu Leu Lys Ala
130                 135                 140

Leu His Leu Gln Gly Gln Asp Met Glu Gln Gln Val Val Phe Ser Met
145                 150                 155                 160

Ser Phe Val Gln Gly Glu Glu Ser Asn Asp Lys Ile Pro Val Ala Leu
                165                 170                 175

Gly Leu Lys Glu Lys Asn Leu Tyr Leu Ser Cys Val Leu Lys Asp Asp
            180                 185                 190

Lys Pro Thr Leu Gln Leu Glu Ser Val Asp Pro Lys Asn Tyr Pro Lys
    195                 200                 205

Lys Lys Met Glu Lys Arg Phe Val Phe Asn Lys Ile Glu Ile Asn Asn
210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
                245                 250                 255

Gln Asp Ile Thr Asp Phe Thr Met Gln Phe Val Ser Ser
            260                 265
```